(12) United States Patent
Carroll et al.

(10) Patent No.: US 9,512,105 B2
(45) Date of Patent: Dec. 6, 2016

(54) 1-SUBSTITUTED 4-ARYLPIPERAZINE AS KAPPA OPIOID RECEPTOR ANTAGONISTS

(71) Applicant: RESEARCH TRIANGLE INSTITUTE, Research Triangle Park, NC (US)

(72) Inventors: Frank I. Carroll, Durham, NC (US); James B. Thomas, Elfand, NC (US); Hernan A. Navarro, Chapel Hill, NC (US); S. Wayne Mascarella, Hillsborough, NC (US); Scott P. Runyon, Hillsborough, NC (US); Chunyang Jin, Apex, NC (US); Chad M. Kormos, Apex, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 14/364,003

(22) PCT Filed: Dec. 10, 2012

(86) PCT No.: PCT/US2012/068751
§ 371 (c)(1),
(2) Date: Jun. 9, 2014

(87) PCT Pub. No.: WO2013/086496
PCT Pub. Date: Jun. 13, 2013

(65) Prior Publication Data
US 2015/0005315 A1    Jan. 1, 2015

Related U.S. Application Data

(60) Provisional application No. 61/568,961, filed on Dec. 9, 2011.

(51) Int. Cl.
*C07D 241/04* (2006.01)
*C07D 401/12* (2006.01)
*C07D 295/13* (2006.01)

(52) U.S. Cl.
CPC ........... *C07D 401/12* (2013.01); *C07D 241/04* (2013.01); *C07D 295/13* (2013.01)

(58) Field of Classification Search
CPC .................................................. C07D 241/04
USPC ............................................... 544/358, 393
See application file for complete search history.

(56) References Cited

U.S. PATENT DOCUMENTS 7,560,463 B2    7/2009    Mitch et al.

FOREIGN PATENT DOCUMENTS

| JP | 2-134374 | 5/1990 |
|---|---|---|
| JP | 9-500883 | 1/1997 |
| JP | 2004-521100 | 7/2004 |
| WO | WO 99/45925 A1 | 9/1999 |
| WO | WO 2007-047737 | 4/2007 |
| WO | 2011 106039 | 9/2011 |

OTHER PUBLICATIONS

STN entry for CAS RN 1208475-53-9 (entered STN on Mar. 10, 2010).*
Examination Report issued Dec. 22, 2015 in Australian Patent Application No. 2012347416.
RN: 1211704-04-9, Chemical Name: Benzamide, 4-phenoxy-N-[2-(4-phenyl-1-piperazinyl)ethyl]—(CA Index Name), Chemical Library Supplier: Ambinter, STN entry date: Mar. 19, 2010, 3 Pages.
Pogozheva, I. D. et al., "Homology Modeling of Opioid Receptor-Ligand Complexes Using Experimental Constraints", The AAPS Journal, vol. 7, No. 2, pp. E434-E448, (2005).
International Search Report Issued Feb. 22, 2013 in PCT/US12/068751 filed Dec. 10, 2012.
Supplementary European Search Report issued Oct. 12, 2015 in Patent Application No. 12 85 6118.0.
Database Registry [Online] Chemical Abstracts Service, Chemical Library, FCH Group, XP002745796, Aug. 15, 2011, 1 Page.
Database Registry [Online] Chemical Abstracts Service, Chemical Library, Ambinter, XP002745797, Mar. 19, 2010, 1 Page.
Database Registry [Online] Chemical Abstracts Service, Chemical Library, Ambinter, XP 002745798, Mar. 16, 2010, 1 Page.
Database Registry [Online] Chemical Abstracts Service, Chemical Library, Ambinter, XP002745799, Mar. 12, 2010, 1 Page.
Database Registry [Online] Chemical Abstracts Service, Chemical Library, Ambinter, XP002745800, Mar. 10, 2010, 1 Page.
Office Action in corresponding Japanese Application No. 2014-546171, dated Jul. 15, 2016. (w/English Translation).
Pogozheva, et al., "Homology Modeling of Opioid Receptor-Ligand Complexes Using Experimental Constraints", The AAPS Journal, 2005, vol. 7, No. 2, pp. 434-448.

* cited by examiner

*Primary Examiner* — Barbara P Badio
*Assistant Examiner* — Sara E Townsley
(74) *Attorney, Agent, or Firm* — Oblon, McClelland, Maier & Neustadt, L.L.P.

(57) ABSTRACT

Provided are compounds represented by the formula: where R, $Y_3$, $R_1$, $R_2$, $R_3$, $R_4$, $R_6$, G, $R_7$, $E_1$, $E_2$, A, B, W, X, Y and Z are as defined herein.

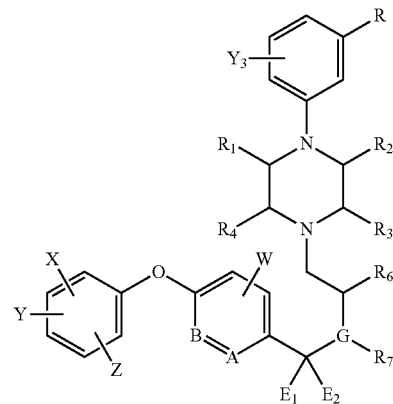

11 Claims, No Drawings

1-SUBSTITUTED 4-ARYLPIPERAZINE AS KAPPA OPIOID RECEPTOR ANTAGONISTS

REFERENCE TO PREVIOUS APPLICATIONS

This application claims benefit to U.S. Provisional Application Ser. No. 61/568,961 filed on Dec. 9, 2011, and incorporated herein by reference.

STATEMENT OF FEDERAL SUPPORT

This invention was made with government support under grant number 2R01DA009045 awarded by the NIH. The government has certain rights in the invention.

BACKGROUND OF THE INVENTION

Field of the Invention

The present invention relates to arylpiperazine compounds which function as opioid receptor antagonists and can be used to treat a variety of disease states.

Description of the Background

The opioid receptors, μ, δ, κ, and the opioid-like receptor ORL-1 belong to the super family of G-protein coupled receptors (GPCRs) that possess seven helical trans-membrane spanning domains in their architecture.[1] The majority of research efforts focused upon this group of proteins has been directed toward the μ receptor since it mediates the actions of both the opiate and opioid analgesics such as morphine and fentanyl, respectively.[2] However, over the years it has become increasingly clear that the entire family of proteins is actively involved in a host of biological processes.[2] Furthermore, the advent of selective antagonists has demonstrated that pharmacotherapeutic opportunities exist via both negative and positive modulation of this receptor family.[3-8]

The opioid receptor system has been extensively studied, and thousands of compounds have been synthesized and evaluated by in vitro binding and functional assays as well as by animal models.[2] An integral part of the effort to characterize the opioid receptor system has been the discovery of potent, pure antagonists. Naloxone (1a) and naltrexone (1b), both competitive antagonists at μ, δ, and κ opioid receptors,[9] have been extensively used as pharmacological tools to identify and characterize opioid systems. Additionally, naloxone is approved to treat heroin overdose and to reverse respiratory depression caused by morphine.[9] Naltrexone is used to treat heroin and alcohol abuse.

In 1978, Zimmerman and co-workers reported the discovery of a structurally unique series of opioid receptor pure antagonists based on N-substituted analogues of 3,4-dimethyl-4-(3-hydroxyphenyl)piperidine (2a, LY272922).[10] Unlike naloxone (1a) and naltrexone (1b) where the antagonist activity is dependent on the N-allyl or N-cyclopropylmethyl substituent, all N-substituted trans-3,4-dimethyl-4-(3-hydroxyphenyl)piperidines (2) including the N-methyl analogue 2b are opioid receptor pure antagonists.[10-14] A few of the more interesting analogues include alvimopan (3), which is an FDA-approved drug for GI motility disorder,[15] LY255,582 (2d),[13,16] which was developed to treat obesity, and the selective κ opioid receptor antagonist JDTic (4),[6-8,17] which shows activity in rat models of depression,[18] anxiety,[19] and stress-induced cocaine relapse.[18] All preclinical studies for JDTic have been completed, and phase 1 clinical studies are underway.

Previous work led to the discovery of 3-(4-substituted piperazin-1-yl)phenols (5) as a new class of opioid receptor antagonists and submitted two patent applications to cover this class of novel opioid receptor antagonist. These studies are presented in a recent publication.[20] These compounds are relatively nonselective opioid receptor antagonists. Thus, their opioid receptor properties are more like those of naloxone (1a), naltrexone (1b), and the originally reported N-substituted 3,4-dimethyl-4-(3-hydroxyphenyl)piperidines.[13]

Previously, the opiate class, represented by naloxone (1a), naltrexone (1b), and the N-substituted 3,4-dimethyl-4-(3-hydroxyphenyl)piperidines, represented by alvimopan, LY255,582, and JDTic, were the only two classes of nonpeptide pure opioid receptor antagonists known. The discovery that 3-(4-substituted piperazin-1-yl)phenols (5) are pure opioid receptor antagonists added a third example of this important class of compounds.

More recently, AZ-MTAB,[21,22] PF-4455242,[23] and LY2456302[23] have been reported as selective κ opioid receptor antagonists. These compounds have a very different structure as compared to the compounds discussed above.

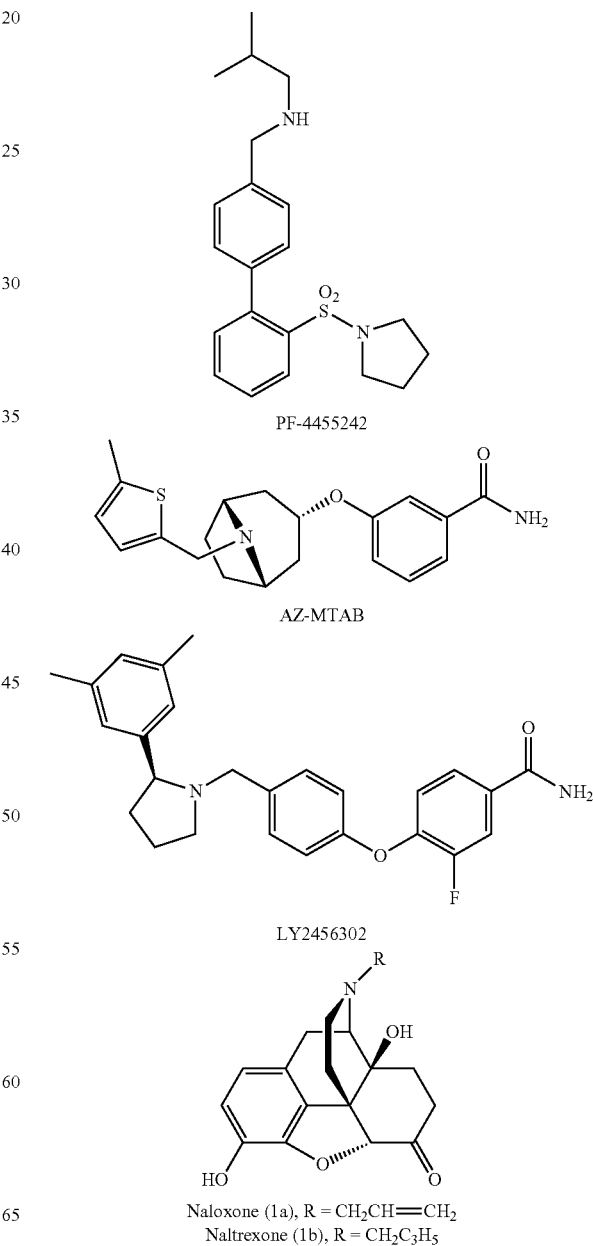

PF-4455242

AZ-MTAB

LY2456302

Naloxone (1a), R = CH$_2$CH=CH$_2$
Naltrexone (1b), R = CH$_2$C$_3$H$_5$

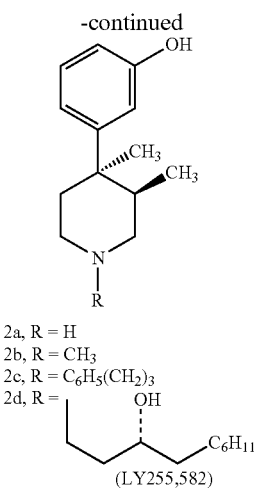

2a, R = H
2b, R = CH₃
2c, R = C₆H₅(CH₂)₃
2d, R =

(LY255,582)

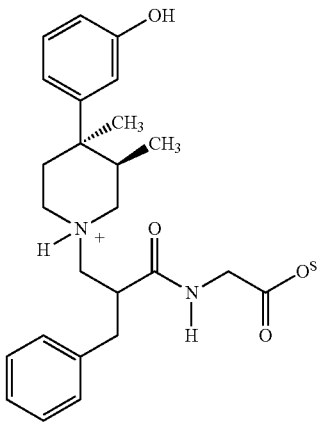

3, LY246736
Alvimopan

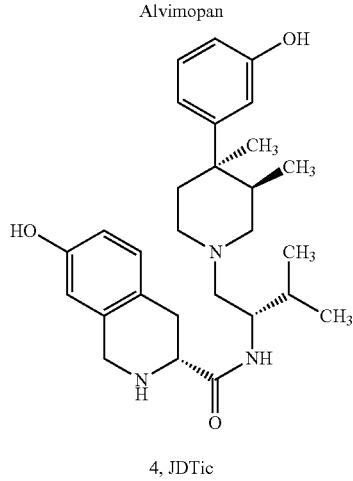

4, JDTic

5

Studies with selective κ opioid antagonists have shown that this system is intimately involved in brain processes that relate to stress, fear, and anxiety as well as reward-seeking behavior. Studies have shown that JDTic (4) and nor-BNI, another κ opioid selective antagonist, dose-dependently reduce fear and stress-induced responses in multiple behavioral paradigms with rodents (immobility in the forced-swim assay,[18,24] reduction of exploratory behavior in the elevated plus maze, and fear-potentiated startle).[19] Furthermore, selective κ antagonists have been shown to reduce stress-induced reinstatement of cocaine self-administration in rats,[18] to block the stress-induced potentiation of cocaine place preference conditioning,[25-27] to decrease dependence-induced ethanol self-administration,[28] to diminish deprivation-induced eating in rats,[29] and to prevent pre-pulse inhibition mediated by U50,488.[30] These observations regarding the behavioral consequences of receptor blockade in several animal tests suggest that κ antagonists will be useful for treating anxiety, depression, schizophrenia, addiction, and eating disorders.

Previously reported non-selective opioid receptor antagonists such as LY255582 have been found to increase metabolic energy consumption and reduce the weight in obese rats while maintaining muscle mass. These reports suggest that opioid receptor antagonists may be useful in preventing, treating, and/or ameliorating the effect of obesity. Eli Lilly and Company has developed new classes of opioid receptor antagonists that interact with the μ, δ, and κ receptors (termed non-selective) as potential pharmacotherapies to treat obesity and related diseases.[31,32] The Lilly patents suggest that their compounds will be useful for the treatment and/or prophylaxis of obesity and related diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example gambling and alcoholism.

In view of the foregoing, there remains a need for improved agents which bind at opioid receptors. There is a particular need for potent and selective κ opioid receptor antagonists relative to the μ and δ opioid receptors.

SUMMARY OF THE INVENTION

The invention described herein is based on the discovery of potent and selective κ opioid receptor antagonist activity with substituted 3-(4-substituted piperazin-1-yl)phenols. Such compounds have remarkably higher affinity for the κ receptor as compared to either the μ receptor or the δ receptor. This heightened selectivity for the κ receptor is particularly significant.

Thus, the present invention relates to a compound represented by the formula:

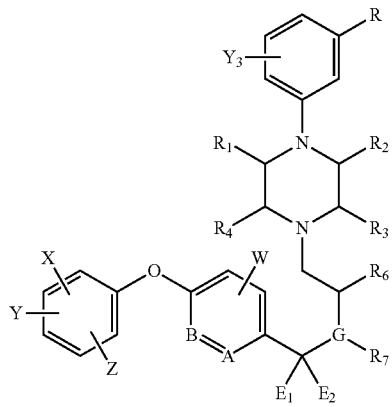

where

R is hydrogen, OH, $OC_{1-6}$ alkyl, $C_{1-8}$ alkyl, $C_{1-8}$ haloalkyl, $C_{2-8}$ alkenyl, $C_{2-8}$ alkynyl, aryl substituted by one or more $Y_1$ groups, $CH_2$-aryl wherein the aryl group is substituted by one or more $Y_1$ groups, $OCOC_{1-8}$ alkyl, $COC_{1-8}$ alkyl, $CONH_2$, $NHCHO$, $NH_2$, $NHSO_2C_{1-8}$ alkyl, or $NHCO_2C_{1-8}$ alkyl;

$Y_3$ is hydrogen, Br, Cl, F, CN, $CF_3$, $NO_2$, $SO_2CH_3$, $SO_2CF_3$, $SO_2NH_2$, $OR_8$, $CO_2R_9$, $C_{1-6}$ alkyl, $NR_{10}R_{11}$, $NHCOR_{12}$, $NHCO_2R_{12}$, $CONR_{13}R_{14}$ or $CH_2(CH_2)_nY_2$;

$R_1$, $R_2$, $R_3$ and $R_4$ are each, independently, one of the following structures:

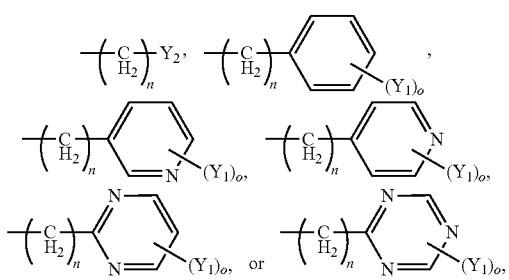

or $R_1$ and $R_2$, $R_2$ and $R_3$ and/or $R_3$ and $R_4$ are bonded together to form a cyclo alkyl group or a bridged heterocyclic ring;

each $Y_1$ is, independently, hydrogen, OH, Br, Cl, F, CN, $CF_3$, $NO_2$, $N_3$, $SO_2CH_3$, $SO_2CF_3$, $SO_2NH_2$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$, or two adjacent $Y_1$ groups form a —O—$CH_2$—O— or —O—$CH_2CH_2$—O- group;

each $Y_2$ is, independently, hydrogen, $CF_3$, $CO_2R_9$, $C_{1-8}$ alkyl, $NR_{10}R_{11}$, $NHCOR_{12}$, $NHCO_2R_{12}$, $CONR_{13}R_{14}$, $CH_2OH$, $CH_2OR_8$, $COCH_2R_9$,

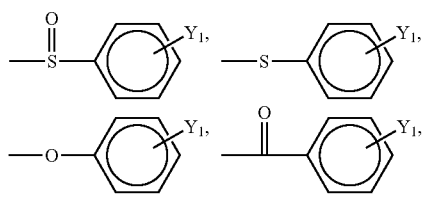

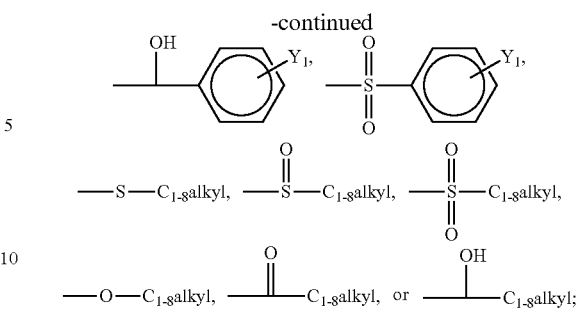

each n is, independently, 0, 1, 2 or 3;
each o is, independently, 0, 1, 2 or 3;
each $R_8$, $R_9$, $R_{10}$, $R_{11}$, $R_{12}$, $R_{13}$ and $R_{14}$ is, independently, hydrogen, $C_{1-8}$ alkyl, $CH_2$-aryl wherein the aryl group is substituted by one or more substituents OH, Br, Cl, F, CN, $CF_3$, $NO_2$, $N_3$, $SO_2CH_3$, $SO_2CF_3$, $SO_2NH_2$, $C_{1-6}$ alkyl, or $CH_2(CH_2)_nY_2'$;

each $Y_2'$ is, independently, hydrogen, $CF_3$, or $C_{1-6}$ alkyl;

$R_6$ is hydrogen, $C_{1-8}$ alkyl, $CO_2C_{1-8}$ alkylaryl substituted by one or more $Y_1$ groups, $CH_2$-aryl substituted by one or more $Y_1$ groups, or $CO_2C_{1-8}$ alkyl;

G is N, O or S, wherein when G is O or S, there is no $R_7$;

$R_7$ is hydrogen, $C_{1-8}$ alkyl, $C_{2-8}$ alkenyl, $C_{2-8}$ alkynyl, $CH_2CO_2C_{1-8}$ alkyl, $CO_2C_{1-8}$ alkyl or $CH_2$-aryl substituted by one or more $Y_1$ groups;

$E_1$ is hydrogen, $C_{1-8}$ alkyl, $C_{2-8}$ alkenyl, or $C_{2-8}$ alkynyl;
$E_2$ is hydrogen, $C_{1-8}$ alkyl, $C_{2-8}$ alkenyl, or $C_{2-8}$ alkynyl;
or $E_1$ and $E_2$ together form =O, =S, or =NH;

A and B are each, independently, CH, CW or N, with the proviso that only one of A and B may be N;

W, X, Y and Z are each, independently, hydrogen, $C_{1-6}$ alkyl, $C_{2-6}$ alkenyl, $C_{2-6}$ alkynyl, $OC_{1-6}$ alkyl, OH, F, Cl, Br, CN, $CF_3$, $NO_2$, $N_3$, $SO_2CH_3$, $SO_2CF_3$, $SO_2NH_2$, $NR_{31}R_{32}$, $NHCOR_{33}$, $NHCO_2R_{34}$, $CONR_{35}R_{36}$, $CH_2(CH_2)_nY_2$, $CH_2O_2C_{1-8}$ alkyl, $CO_2C_{1-8}$ alkyl or $C(=NH)NR_{37}R_{38}$;

$R_{31}$, $R_{32}$, $R_{33}$, $R_{34}$, $R_{35}$, $R_{36}$, $R_{37}$ and $R_{38}$ are, independently, hydrogen, $C_{1-6}$ alkyl, $C_{2-6}$ alkenyl, $C_{2-6}$ alkynyl, $CH_2$-aryl substituted by one or more substituents OH, Br, Cl, F, CN, $CF_3$, $NO_2$, $N_3$, $SO_2CH_3$, $SO_2CF_3$, $SO_2NH_2$, $C_{1-6}$ alkyl, or $CH_2(CH_2)_nY_2'$;

or a pharmaceutically acceptable salt thereof.

The present invention also includes pharmaceutical compositions, which comprise the opioid receptor antagonist described above and a pharmaceutically acceptable carrier.

The present invention also includes a method of antagonizing opioid receptors, comprising administering an effective amount of the opioid receptor antagonist discussed above to a subject in need thereof.

The present invention also includes a method of treating drug addiction, drug abuse, depression, anxiety, schizophrenia, obesity and eating disorders, comprising administering an effective amount of the opioid receptor antagonist discussed above to a subject in need thereof.

The present invention also includes a method of treating alcohol addiction, nicotine addiction, cocaine addiction and methamphetamine addiction, comprising administering an effective amount of the opioid receptor antagonist discussed above to a subject in need thereof.

The present invention also includes a method of treating diabetes, diabetic complications, diabetic retinopathy, sexual/reproductive disorders, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders and addictive behaviors, comprising administering an effective amount of the opioid receptor antagonist discussed above to a subject in need thereof.

A more complete appreciation of the invention and many of the attendant advantages thereof will be readily obtained as the same becomes better understood by reference to the following Figures in conjunction with the detailed description below.

DETAILED DESCRIPTION OF THE INVENTION

A broad description of the invention is provided in the Summary section above.

In one embodiment of the invention, R is hydrogen, OH, $OC_{1-3}$ alkyl, $C_{1-4}$ alkyl, $C_{1-4}$ haloalkyl, $C_{2-4}$ alkenyl, $C_{2-4}$ alkynyl, aryl substituted by one or more groups $Y_1$, $CH_2$-aryl wherein the aryl group is substituted by one or more $Y_1$ groups, $OCOC_{1-4}$ alkyl, $COC_{1-4}$ alkyl, $CONH_2$, NHCHO, $NH_2$, $NHSO_2C_{1-4}$ alkyl, or $NHCO_2C_{1-4}$ alkyl; and $Y_3$ is hydrogen, Br, Cl, F, CN, $CF_3$, $NO_2$, $SO_2CH_3$, $SO_2CF_3$, $SO_2NH_2$, $OR_8$, $CO_2R_9$, $C_{1-3}$ alkyl, $NR_{10}R_{11}$, $NHCOR_{12}$, $NHCO_2R_{12}$, $CONR_{13}R_{14}$ or $CH_2(CH_2)_nY_2$. In a preferred embodiment, $Y_3$ is hydrogen.

In another embodiment of the invention, $R_1$, $R_2$, $R_3$ and $R_4$ are each, independently, one of the following structures:

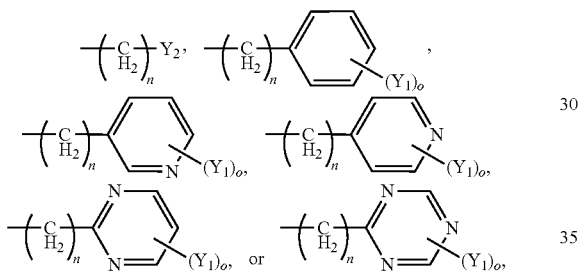

or $R_1$ and $R_2$, $R_2$ and $R_3$ and/or $R_3$ and $R_4$ are bonded together to 5 to 7 membered alkyl group or a bridged heterocyclic ring.

In another embodiment of the invention, at least one of $R_1$, $R_2$, $R_3$ and $R_4$ is other than hydrogen.

In another embodiment of the invention, $R_1$, $R_2$, $R_3$ and $R_4$ are each, independently, hydrogen or methyl.

In another embodiment of the invention, R is hydrogen, OH, $OCH_3$, or $OCF_3$.

In another embodiment of the invention, $R_1$, $R_2$, $R_3$ and $R_4$ are each, independently, hydrogen or methyl, wherein at least one of $R_1$, $R_2$, $R_3$ and $R_4$ is methyl. In a preferred embodiment, $R_2$ is methyl.

$R_6$ may be hydrogen, $C_{1-8}$ alkyl, $CO_2C_{1-8}$ alkylaryl substituted by one or more $Y_1$ groups, $CH_2$-aryl substituted by one or more $Y_1$ groups, or $CO_2C_{1-8}$ alkyl. In a preferred embodiment, $R_6$ is an isopropyl group.

In one embodiment of the invention, G is N.

In a preferred embodiment of the present invention, $E_1$ and $E_2$ together form =O.

The group W is an optional substituent on the phenyl group to which it is attached. One skilled the art will recognize that any carbon atom in that phenyl group, other than the carbon atoms which are bonded to the —O— and —C($E_1$)($E_2$)- groups may be CW. In a preferred embodiment, W is hydrogen.

As noted above, the ring to which W is attached may contain one nitrogen in the ring, represented by A or B. However, only one of A and B may be nitrogen. An A or B that is not nitrogen may be CH or CW. Thus, in one embodiment, both A and B may be CH. In another embodiment, one of A and B is CW and the other is CH. In another embodiment, one of A and B is N and the other is CH or CW. A and B are not both N, however.

The groups X, Y and Z are optional substituents on the ring to which those groups are attached. These groups may be attached to any carbon atom of the ring. In one embodiment, each of X, Y and Z is a hydrogen. In another embodiment, one of X, Y and Z is other than a hydrogen atom as defined above. In another embodiment, two of X, Y and Z is other than a hydrogen atom as defined above. In another embodiment, each of X, Y and Z is other than a hydrogen atom as defined above.

In another embodiment of the invention, the opioid receptor antagonist is represented by the formula:

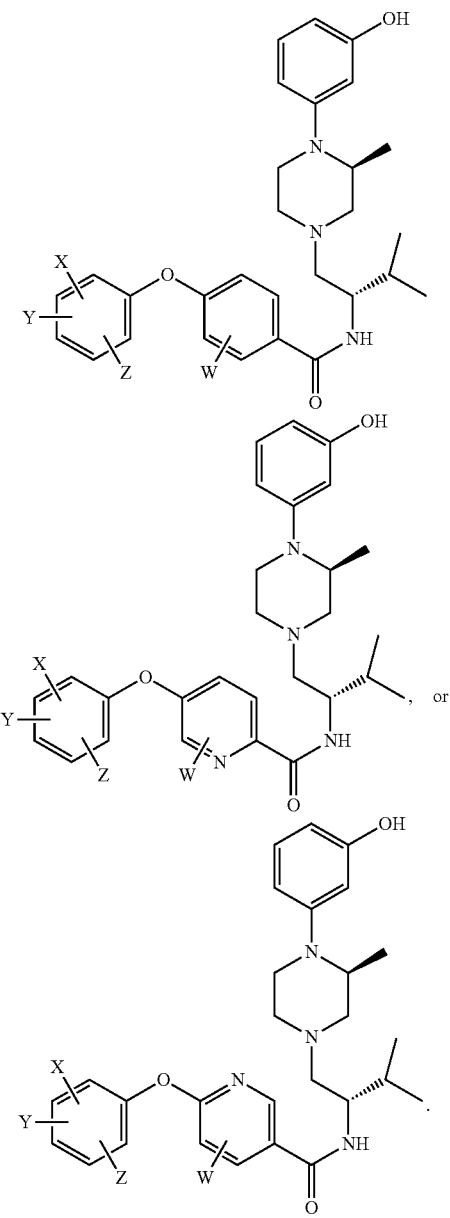

where W, X, Y and Z are as defined above.

In another embodiment of the invention, W, X, Y and Z in any of the compounds discussed above, are, independently, hydrogen, $C_{1-3}$ alkyl, $OC_{1-3}$ alkyl, F, OH, Br, Cl, CN, $CF_3$, $NO_2$, $SO_2CH_3$, $SO_2CF_3$ or $SO_2NH_2$.

In another embodiment of the invention, W, X, Y and Z of any compound as described herein are, independently, hydrogen, methyl, methoxy, F, Cl or OH.

The following Examples list specific compounds within the scope of the invention, although it will be understood that such compounds are not meant to limit the scope of the invention defined herein. Rather, such compounds are intended to be exemplificative of the present invention. Examples of compounds within the scope of the present invention are represented by the formula:

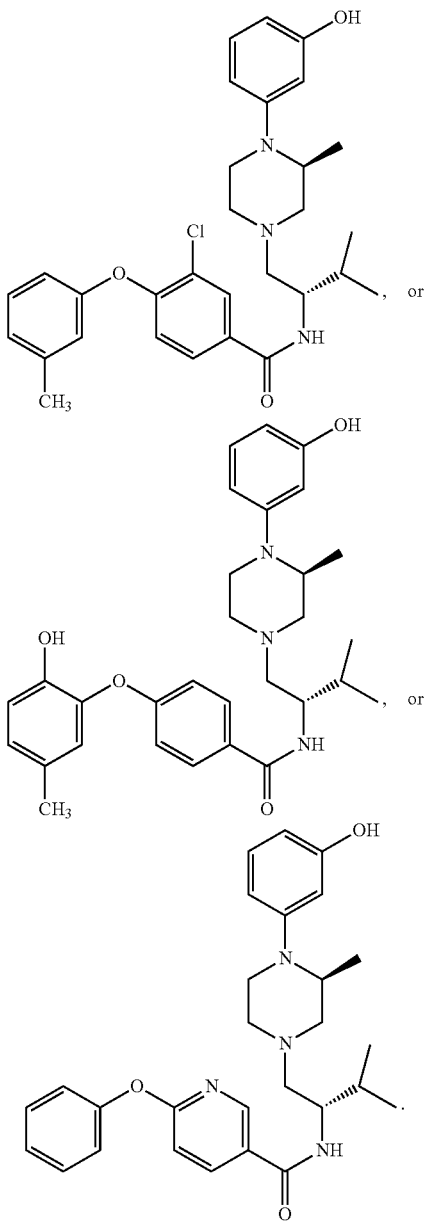

In another embodiment of the invention, the opioid receptor antagonist is a pharmaceutically acceptable salt.

In another preferred embodiment of the present invention, the opioid receptor antagonists are as described in the following Examples section.

The present invention includes any and all combination of the different structural groups defined above, including those combinations not specifically set forth above.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms. Representative examples include methyl, ethyl, propyl and cyclohexyl.

As used throughout this disclosure, the terms "haloalkyl group" or "haloalkyl radical" encompass all structural isomers thereof, such as linear, branched and cyclic groups and moieties. Unless stated otherwise, all haloalkyl groups described herein may have 1 to 8 carbon atoms, inclusive of all specific values and subranges therebetween, such as 2, 3, 4, 5, 6, or 7 carbon atoms. A $C_{1-2}$ haloalkyl group is particularly preferred. At least one hydrogen atom is replaced by a halogen atom, i.e., fluorine, chlorine, bromine or iodine. In one embodiment, all of the hydrogen atoms are replaced with halogen atoms. Fluorine is preferred. Perfluoroalkyl groups are particularly preferred. Examples of haloalkyl groups include trifluoromethyl (—$CF_3$) and perfluoroethyl (—$CF_2CF_3$).

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom. Unless stated otherwise, all alkenyl and alkynyl groups described herein may have 2 to 8 carbon atoms, inclusive of all specific values and subranges therebetween, such as 3, 4, 5, 6, or 7 carbon atoms. Preferred examples include —CH=$CH_2$, —$CH_2$CH=$CH_2$, —C≡CH and —$CH_2$C≡CH.

The aryl group is a hydrocarbon aryl group, such as a phenyl, naphthyl, phenanthryl, anthracenyl group, which may have one or more $C_{1-4}$ alkyl group substituents.

The compounds of the present invention may be in the form of a pharmaceutically acceptable salt via protonation of the amines with a suitable acid. The acid may be an inorganic acid or an organic acid. Suitable acids include, for example, hydrochloric, hydroiodic, hydrobromic, sulfuric, phosphoric, citric, acetic, fumaric, tartaric, and formic acids.

The opioid receptor selectivity may be determined based on the binding affinities at the receptors indicated or their selectivity in opioid functional assays.

The compounds of the present invention may be used to bind opioid receptors. Such binding may be accomplished by contacting the receptor with an effective amount of the inventive compound. Of course, such contacting is preferably conducted in an aqueous medium, preferably at physiologically relevant ionic strength, pH, etc. Receptor antagonism is the preferred mode of action of the compounds described herein.

The inventive compounds may also be used to treat patients having disease states which are ameliorated by binding opioid receptors or in any treatment wherein temporary suppression of the kappa opioid receptor system is desired. Such diseases states include opiate addiction (such as heroin addiction), cocaine, nicotine, or ethanol addiction. The compounds of the present invention may also be used as cytostatic agents, as antimigraine agents, as immunomodulators, as immunosuppressives, as antiarthritic agents, as antiallergic agents, as virucides, to treat diarrhea, as antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds can be used in the treatment of Parkinson's disease as an adjunct to L-dopa for treatment of dyskinesia associated with the L-dopa treatment.

The compounds of the present invention are particularly useful for treating addiction, such as addiction to cocaine, alcohol, methamphetamine, nicotine, heroin, and other drugs of abuse. With respect to nicotine, the compounds of the present invention are also useful in treating nicotine withdrawal effects.

The compounds may be administered in an effective amount by any of the conventional techniques well-established in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see *Kirk-Othmer Encyclopedia of Chemical Technology*, Fourth Edition, Vol. 18, 1996, pp. 480-590, incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Suitable compositions containing the present compounds further comprise a physiologically acceptable carrier, such as water or conventional pharmaceutical solid carriers, and if desired, one or more buffers and other excipients.

The compounds of the invention may be synthesized by, for example, the schemes shown in the following Examples. Those skilled in the art will appreciate that the synthesis of the exemplified compounds can readily be adapted for the preparation of other compounds within the scope of general formula described above.

EXAMPLES

Having generally described this invention, a further understanding can be obtained by reference to certain specific examples which are provided herein for purposes of illustration only and are not intended to be limiting unless otherwise specified.

The synthesis and activity of exemplary compounds of the present invention are described below.

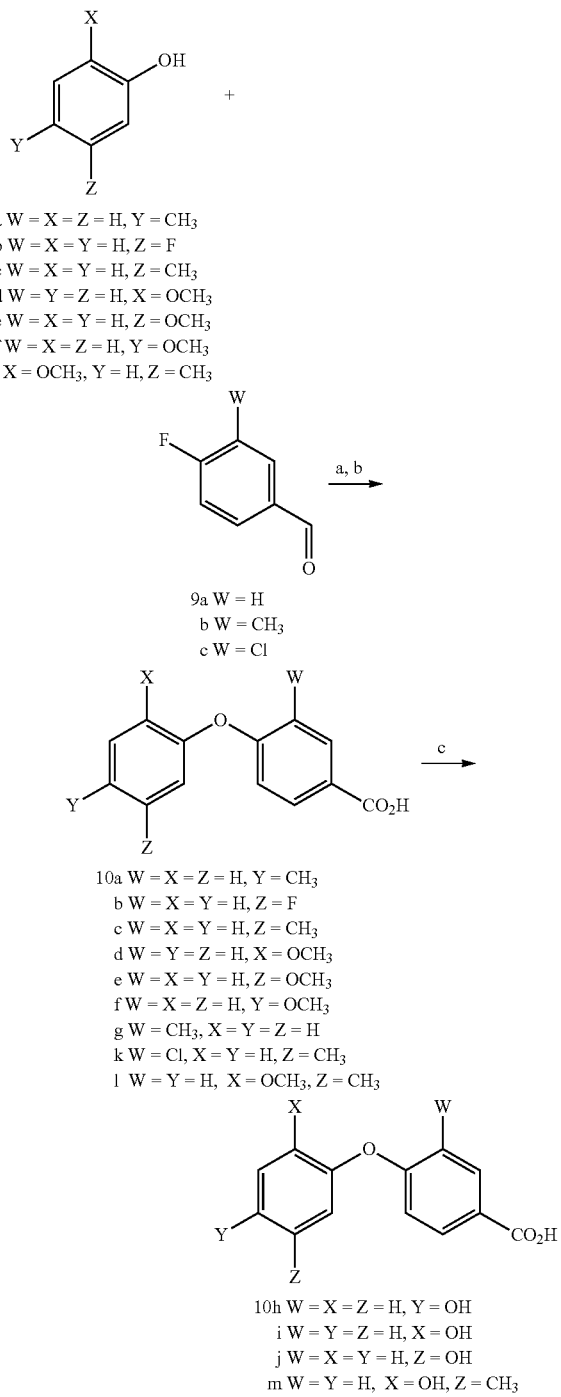

Scheme 1

Reagents: (a) $K_2CO_3$ or KOH, DMF, 175° C., sealed tube; (b) $CrO_3$, acetone, room temperature; (c) 48% HBr, AcOH, reflux.

The substituted 4-phenoxybenzoic acids 10a-10m were synthesized in accordance with the reaction sequence, shown in Scheme 1. Phenols 8a-8g were allowed to react with 4-fluorobenzaldehyde, 4-fluoro-3-methylbenzaldehyde, or 3-chloro-4-fluorobenzaldehyde at high temperature in the presence of potassium carbonate or potassium hydroxide to yield diaryl ethers, which were oxidized with Jones reagent to the corresponding acids 10a-10g, 10k and 10l. With the compounds where X, Y, or Z=$OCH_3$, treatment with refluxing 48% HBr yielded the corresponding hydroxy-substituted acids 10h-10j and 10m.

phenol gave aryl ether 20, which upon saponification with lithium hydroxide yielded the desired carboxylic acid 21.

Scheme 2

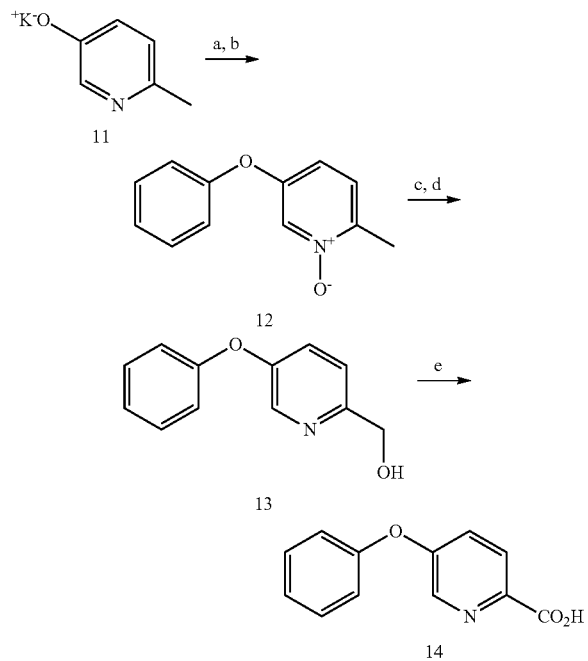

Reagents: (a) iodobenzene, copper dust, DMF, reflux; (b) mCPBA, CH$_2$Cl$_2$, room temperature; (c) Ac$_2$O, AcOH, 150° C., sealed tube; (d) K$_2$CO$_3$, CH$_3$OH, H$_2$O, room temperature; (e) KMnO$_4$, acetone, 50° C.

Acid 14 was synthesized by the route, shown in Scheme 2. The Ullmann ether condensation of pyridine 11 with iodobenzene, followed by oxidation with mCPBA yielded the pyridine N-oxide 12. Treatment of 12 with acetic anhydride at 150° C. in a sealed tube and hydrolysis of the resulting intermediate with potassium carbonate in aqueous methanol afforded alcohol 13. Oxidation of 13 with potassium permanganate provided acid 14.

Scheme 3

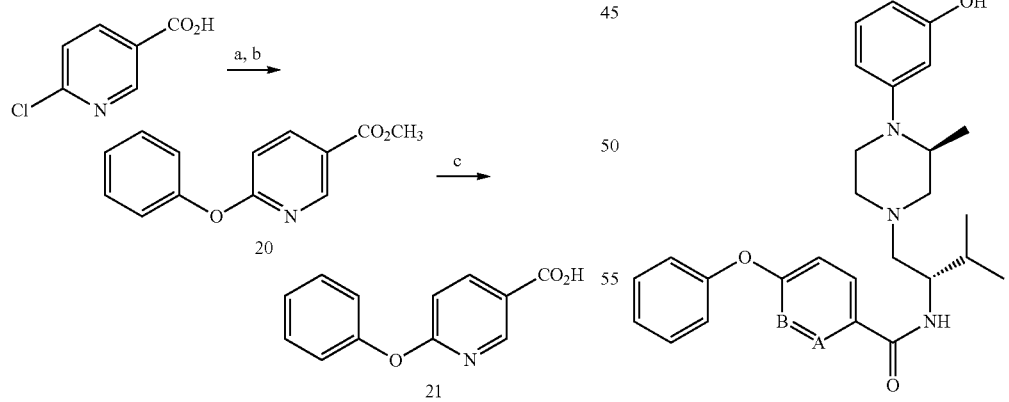

Reagents: (a) TMSCHN$_2$, toluene, MeOH; (b) phenol, Cs$_2$CO$_3$, CH$_3$CN, reflux; (c) LiOH, MeOH, H$_2$O.

Acid 21 was prepared according to the sequence illustrated in Scheme 3. The methyl ester of 6-chloronicotinic acid was prepared using trimethylsilyldiazomethane in toluene and methanol. Nucleophilic aromatic substitution with Scheme 4

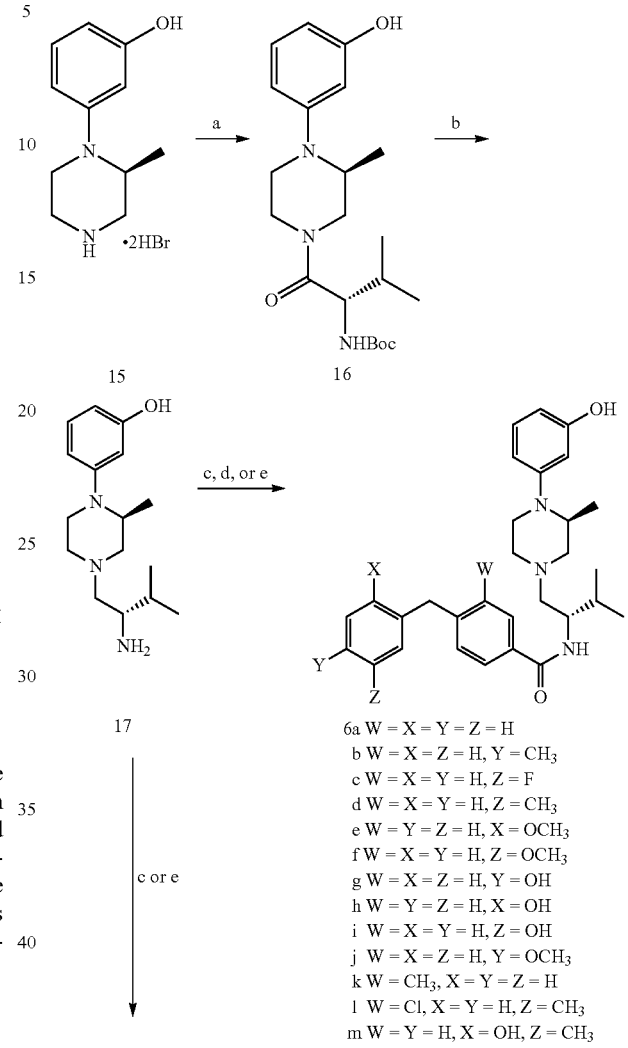

6a W = X = Y = Z = H
b W = X = Z = H, Y = CH$_3$
c W = X = Y = H, Z = F
d W = X = Y = H, Z = CH$_3$
e W = Y = Z = H, X = OCH$_3$
f W = X = Y = H, Z = OCH$_3$
g W = X = Z = H, Y = OH
h W = Y = Z = H, X = OH
i W = X = Y = H, Z = OH
j W = X = Z = H, Y = OCH$_3$
k W = CH$_3$, X = Y = Z = H
l W = Cl, X = Y = H, Z = CH$_3$
m W = Y = H, X = OH, Z = CH$_3$

7a A = N, B = CH
7b A = CH, B = N

Reagents: (a) N-Boc-L-valine, HBTU, Et$_3$N, CH$_3$CN, room temperature; (b) BH$_3$•THF, room temperature, then conc. HCl, reflux; (c) phenoxybenzoic acid or 14, HBTU, Et$_3$N, CH$_3$CN, room temperature; (d) 10a-10e, BOP, Et$_3$N, CH$_2$Cl$_2$, room temperature; (e) 10f-10j, or 14 or 21, EDC•HCl, Et$_3$N, CH$_2$Cl$_2$, room temperature.

Compounds 6a-6m, 7a, and 7b were synthesized following the reaction sequence, outlined in Scheme 4. The starting piperazine 15 was synthesized according to the reported method.[20] Coupling of 15 with N-Boc-L-valine using HBTU afforded amide 16, which was reduced with borane in THF, followed by HCl treatment, to give amine 17 Amine 17 was coupled with the appropriate acid using HBTU, BOP or EDC.HCl to yield target compounds 6a-6m, 7a, and 7b. Compounds 19a-p were synthesized by procedures similar to those used for the synthesis of 6a-m as outlined in Scheme 5.

Scheme 5

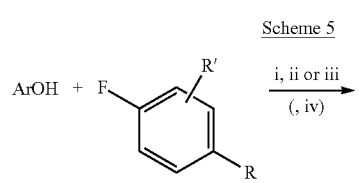

R = CHO or CN
R′ = CH$_3$, OCH$_3$, or Cl

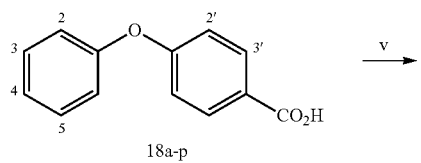

18a-p a: 2-F           i: 3-CH$_3$, 2′-OH
b: 3-CF$_3$      j: 3-CH$_3$, 3′-CH$_3$
c: 3-Cl          k: 3-CH$_3$, 3′-OCH$_3$
d: 3-Br          l: 3-CH$_3$, 3′-OH
e: 2-OH, 3-CH$_3$   m: 2-OH, 2′-OCH$_3$
f: 3-CH$_3$, 5-CH$_3$   n: 2-OH, 2′-Cl
g: 3-CH$_3$, 2′-CH$_3$  o: 2-OH, 5-CH$_3$, 2′-OCH$_3$
h: 3-CH$_3$, 2′-OCH$_3$ p: 2-OH, 5-CH$_3$, 2′-Cl

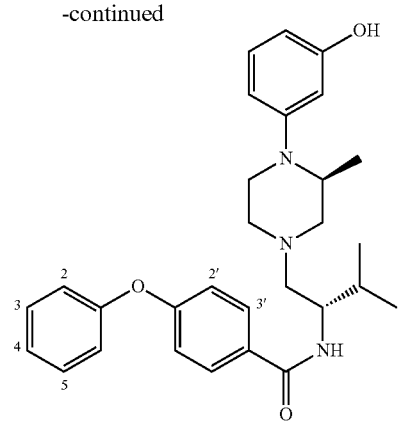

19a-p

Reagents and conditions: (i) KOH, DMF, 175° C., 20 min; (ii) CrO$_3$, aq. H$_2$SO$_4$, acetone; (iii) aq. KOH, reflux; (iv) HBr, AcOH, reflux; (v) 17, EDC•HCl, NEt$_3$.

Biological Activity

Measures of opioid receptor antagonism and specificity were obtained by monitoring the ability of selected test compounds to inhibit stimulation of [$^{35}$S]GTPγS binding produced by the selective agonists (D-Ala$^2$,MePhe$^4$,Gly-ol$^5$) enkephalin (DAMGO, μ receptor) cyclo[D-Pen$^2$,D-Pen$^5$] enkephalin (DPDPE, δ) and 5,7,8-(−)-N-methyl-N-[7-(1-pyrrolidinyl)-1-oxaspiro[4,5]dec-8-yl]benzeneacetamide (U69,593, κ) in cloned human receptors. The data is presented in Table 1.

Compounds 6a-6m, 7a, and 7b as well as 19a-p show high efficacy (low K$_e$ values) for the κ opioid receptor in the [$^{35}$S]GTPγS in vitro functional assay, particularly 6a, 6b, 6d, 6f, 6j, 6k, 6l, 19a, and 19c-j. In addition, 6a, 6d, 6h, 6l, 19e, 19g, and 19h have greater than 60 and 131 selectivity for the κ receptor relative to the μ and δ receptors.

The compounds of the present invention are potent κ opioid receptor antagonists in an in vitro functional test. Some of the compounds showed high selectivity for the κ relative to the μ and δ opioid receptors.

TABLE 1

Inhibition of Agonist Stimulated [$^{35}$S]GTPγS Binding in Cloned Human μ, δ, and κ-Opioid Receptors for Compounds

| RTI-5989- | Comp | W, X, Y, Z | μ, DAMGO K$_e$ (nM)$^a$ | δ, DPDPE K$_e$ (nM)$^a$ | κ, U69,593 K$_e$ (nM)$^a$ | μ/κ | δ/κ |
|---|---|---|---|---|---|---|---|
| 305 | 6a | H, H, H, H | 51 ± 14.9 | 570 ± 79 | 0.85 ± 0.35 | 60 | 671 |
| 320 | 6b | H, H, CH$_3$, H | 20 ± 6 | 188 ± 33 | 0.69 ± 0.25 | 29 | 275 |
| 321 | 6c | H, H, H, F | 30 ± 9.0 | 174 ± 4.5 | 1.48 ± 0.51 | 16 | 118 |
| 322 | 6d | H, H, H, CH$_3$ | 18 ± 6 | 62 ± 20 | 0.18 ± 0.06 | 100 | 344 |
| 323 | 6e | H, CH$_3$O, H, H | 127 ± 78 | 869 ± 205 | 5.60 ± 1.41 | 25 | 155 |

TABLE 1-continued

Inhibition of Agonist Stimulated [$^{35}$S]GTPγS Binding in Cloned Human μ, δ, and κ-Opioid Receptors for Compounds

| RTI-5989- | Comp | W, X, Y, Z | μ, DAMGO $K_e$ (nM)$^a$ | δ, DPDPE $K_e$ (nM)$^a$ | κ, U69,593 $K_e$ (nM)$^a$ | μ/κ | δ/κ |
|---|---|---|---|---|---|---|---|
| 324 | 6f | H, H, H, CH$_3$O | 33 ± 14 | 1502 ± 412 | 0.63 ± 0.13 | 52 | 2384 |
| 325 | 6g | H, H, OH, H | 71 ± 19 | 1696 ± 377 | 8.6 ± 3.7 | 8 | 1.97 |
| 326 | 6h | H, OH, H, H | 125 ± 10 | 960 ± 224 | 1.06 ± 0.26 | 146 | 906 |
| 327 | 6i | H, H, H, OH | 69 ± 14 | 625 ± 121 | 1.85 ± 0.51 | 37 | 338 |
| 328 | 6j | H, H, CH$_3$O, H | 17 ± 5 | 1383 ± 1049 | 0.60 ± 0.19 | 28 | 2305 |
| 329 | 6k | CH$_3$, H, H, H | 15 ± 2 | 435 ± 143 | 0.63 ± 0.19 | 24 | 691 |
| 332 | 6l | Cl, H, H, CH$_3$ | 43 ± 10 | 1100 ± 262 | 0.29 ± 0.13 | 148 | 3793 |
| 333 | 6m | H, OH, H, H, CH$_3$ | 65 ± 18 | 93 ± 27 | 0.61 ± 0.27 | 106 | 152 |
| 316 | 7a | — | 101 ± 16 | 2023 ± 678 | 2.8 ± 1.2 | 36 | 723 |
| 331 | 7b | — | 60 ± 11 | 1790 ± 63 | 1.6 ± 0.3 | 38 | 1119 |

$^{(a)}$None of the compounds showed agonist activity at 10 μM.

Experimental Procedures

Melting points were determined using a MEL-TEMP II capillary melting point apparatus and are uncorrected. Nuclear magnetic resonance ($^1$H NMR and $^{13}$C NMR) spectra were obtained on a Bruker Avance DPX-300 MHz NMR spectrometer or a Varian Unity Inova 500 MHz NMR spectrometer. Chemical shifts are reported in parts per million (ppm) with reference to internal solvent. Mass spectra (MS) were run on a Perkin-Elmer Sciex API 150 EX mass spectrometer equipped with APCI (atmospheric pressure chemical ionization) or ESI (turbospray) sources or on a Hewlett Packard 5989A instrument by electron impact. Elemental analyses were performed by Atlantic Microlab Inc., Atlanta, Ga. Optical rotations were measured on an AutoPol III polarimeter, purchased from Rudolf Research. Analytical thin-layer chromatography (TLC) was carried out using EMD silica gel 60 F$_{254}$ TLC plates. TLC visualization was achieved with a UV lamp or in an iodine chamber. Flash column chromatography was done on a CombiFlash Companion system using Isco prepacked silica gel columns or using EM Science silica gel 60 Å (230-400 mesh). Solvent system: 80CMA=80:18:2 CHCl$_3$:MeOH:conc. NH$_4$OH. Unless otherwise stated, reagent-grade chemicals were obtained from commercial sources and were used without further purification. All moisture and air-sensitive reactions and reagent transfers were carried out under dry nitrogen.

General Procedures for the Preparation of 3-[4-(Substituted piperazin-1-yl)]-phenols (6a-6m, 7a, and 7b)

General Procedure A. The appropriate phenol (5.10 mmol) and KOH (5.10 mmol) were dissolved in DMF (3 mL) before the appropriate 4-fluorobenzaldehyde (5.00 mmol) was added. The solution was heated in a sealed tube to 175° C. for 20 min, poured into H$_2$O (25 mL) and extracted with Et$_2$O (75 mL). The organic layer was washed with H$_2$O (25 mL), brine (10 mL) and dried (Na$_2$SO$_4$). The crude residue resulting from concentration was dissolved in acetone (25 mL) and treated with Jones reagent (3 mL, 0.1 M CrO$_3$ in aqueous H$_2$SO$_4$). Upon completion by TLC, isopropanol (3 mL) was added and the reaction mixture was concentrated. The residue was dissolved in 5% aqueous NaOH, filtered, and the filtrate was acidified with 50% H$_2$SO$_4$ and extracted with EtOAc (3×25 mL). The combined EtOAc extracts were dried (Na$_2$SO$_4$) and concentrated to afford the desired substituted 4-phenoxybenzoic acid.

General Procedure B. To a solution of the appropriate acid (0.05 mmol) and BOP reagent (0.05 mmol) in CH$_2$Cl$_2$ (10 mL) was added piperazine 17 (0.05 mmol) in THF (2 mL) and Et$_3$N (25 μL). After 12 h, the residue resulting from concentration was purified by flash column chromatography on silica gel using an EtOAc gradient in hexane. The residue from concentration of the combined desired fractions was dissolved in CH$_2$Cl$_2$ and treated with dry HCl in Et$_2$O. Removal of the solvent, followed by trituration of the residue with Et$_2$O yielded the desired product as the dihydrochloride salt.

General Procedure C. To a solution of the appropriate acid (0.12 mmol) and piperazine 17 (0.12 mmol) in CH$_2$Cl$_2$ (5 mL) was added HOBt (10 mol %), EDC.HCl (0.12 mmol) and Et$_3$N (40 μL). After 12 h, the residue resulting from concentration was purified by flash column chromatography on silica gel using an EtOAc gradient in hexane. The residue from concentration of the combined desired fractions was dissolved in CH$_2$Cl$_2$ and treated with dry HCl in Et$_2$O. Removal of the solvent, followed by trituration of the residue with Et$_2$O yielded the desired product as the dihydrochloride salt.

4-(4-Methylphenoxy)benzoic Acid (10a) was prepared according to the general procedure of Evans et al. from 4-tolylboronic acid and 4-hydroxybenzoic acid.[34] Yield 13%. ¹H NMR (CDCl₃) δ 8.05 (d, 2H, J=8.8 Hz), 7.20 (d, 2H, J=8.4 Hz), 6.98 (d, 4H, J=8.7 Hz), 2.37 (s, 3H).

4-(3-Fluorophenoxy)benzoic Acid (10b) was prepared from 4-(3-fluorophenoxy)-benzaldehyde according to general procedure A. Yield 80%. ¹H NMR (CDCl₃) δ 8.08 (d, 2H, J=8.8 Hz), 7.35 (q, 1H, J=7.7 Hz), 7.05 (d, 2H, J=8.7 Hz), 6.96-6.76 (m, 3H).

4-(3-Methylphenoxy)benzoic Acid (10c) was prepared according to general procedure A. Yield 46%. ¹H NMR (CDCl₃) δ 8.06 (d, 2H, J=8.0 Hz), 7.28 (t, 1H, J=7.7 Hz), 7.02 (d, 1H, J=7.7 Hz), 7.00 (d, 2H, J=8.1 Hz), 6.90 (s, 1H), 6.88 (d, 1H, J=8.0 Hz), 2.37 (s, 3H).

4-(2-Methoxyphenoxy)benzoic Acid (10d) was prepared according to general procedure A. Yield 31%. ¹H NMR (CDCl₃) δ 7.99 (d, 2H, J=8.5 Hz), 7.22 (t, 1H, J=7.8 Hz), 7.10-6.95 (m, 3H), 6.91 (d, 2H, J=8.4 Hz), 3.80 (s, 3H).

4-(3-Methoxyphenoxy)benzoic Acid (10e) was prepared according to general procedure A. Yield 12%. ¹H NMR (CDCl₃) δ 8.08 (d, 2H, J=7.7 Hz), 7.29 (t, 1H, J=8.1 Hz), 7.02 (d, 2H, J=7.7 Hz), 6.75 (d, 1H, J=7.4 Hz), 6.66 (d, 1H, J=7.4 Hz), 6.64 (s, 1H).

4-(4-Methoxyphenoxy)benzoic Acid (10f) was prepared according to general procedure A. Yield 23%. ¹H NMR (CDCl₃) δ 8.05 (d, 2H, J=8.3 Hz), 7.11-6.85 (m, 6H), 3.83 (s, 2H).

3-Methyl-4-phenoxybenzoic Acid (10g) was prepared according to general procedure A. Yield 30%. ¹H NMR (CDCl₃) δ 7.93 (d, 2H, J=9.0 Hz), 7.44-6.74 (m, 6H), 2.35 (s, 3H).

4-(4-Hydroxyphenoxy)benzoic Acid (10h) was prepared by refluxing 4-(4-methoxyphenoxy)benzoic acid 10f (100 mg) in 48% HBr (4 mL) and AcOH (4 mL) for 12 h. Extraction with CH₂Cl₂, followed by concentration from toluene afforded 10h (29%). ¹H NMR (CDCl₃) δ 7.99 (d, 2H, J=9.0 Hz), 7.00-6.80 (m, 6H).

4-(2-Hydroxyphenoxy)benzoic Acid (10i) was prepared by refluxing 4-(2-methoxyphenoxy)benzoic acid 10d (100 mg) in 48% HBr (4 mL) and AcOH (4 mL) for 12 h. Extraction with CH₂Cl₂, followed by concentration from toluene afforded 10i (46%). ¹H NMR (CDCl₃) δ 8.03 (d, 2H, J=8.9 Hz), 7.17-7.04 (m, 2H), 7.01 (d, 2H, J=8.9 Hz), 6.97 (d, 1H, J=1.5 Hz), 6.94-6.86 (m, 1H).

4-(3-Hydroxyphenoxy)benzoic Acid (10j) was prepared by refluxing 4-(3-methoxyphenoxy)benzoic acid 10e (120 mg) in 48% HBr (5 mL) and AcOH (5 mL) for 12 h. Extraction with CH₂Cl₂, concentrated, followed by flash column chromatography on silica gel using an EtOAc gradient in hexane afforded 10j (96 mg, 79%). ¹H NMR (CD₃OD) δ 8.00 (d, 2H, J=9.0 Hz), 7.20 (t, 1H, J=8.1 Hz), 6.99 (d, 2H, J=8.8 Hz), 6.67-6.60 (m, 1H), 6.55-6.47 (m, 2H).

3-Chloro-4-(3-methylphenoxy)benzoic Acid (10k) was prepared according to general procedure A. Yield 27%. ¹H NMR (CDCl₃) δ 8.20 (d, 1H, J=2.0 Hz), 7.89 (dd, 1H, J=8.7, 2.1 Hz), 7.29 (t, 1H, J=7.9 Hz), 7.03 (d, 1H, J=7.5 Hz), 6.91-6.84 (m, 3H), 2.37 (s, 3H).

4-(5-Methyl-2-methoxyphenoxy)benzoic Acid (10l) was prepared according to general procedure A. Yield 45%.

4-(2-Hydroxy-5-methylphenoxy)benzoic Acid (10m) was prepared by refluxing crude 4-(5-methyl-2-methoxyphenoxy)benzoic acid 10l (288 mg) in 48% HBr (10 mL) for 8 h. Extraction with EtOAc, concentrated, followed by flash column chromatography on silica gel using a CH₃OH gradient in CH₂Cl₂ afforded 10m (220 mg, 81%). ¹H NMR (CD₃OD) δ 7.97 (d, 2H, J=8.0 Hz), 6.96-6.80 (m, 5H), 2.25 (s, 3H); MS (ESI) m/z 243.3 (M−H)⁻.

2-Methyl-5-phenoxypyridine N-Oxide (12). KOH (605 mg, 9.20 mmol) and 5-hydroxy-2-methylpyridine (1.00 g, 9.20 mmol) were dissolved in EtOH then concentrated to dryness. DMF (20 mL), copper dust (640 mg, 10.0 mmol), and iodobenzene (0.95 mL, 8.50 mmol) were added. The heterogeneous reaction was refluxed for 48 h then filtered through Celite and concentrated. Flash column chromatography of the crude product on silica gel using an EtOAc gradient in hexane afforded 5-phenoxy-2-picoline (0.94 g, 55%) as an oil. To a solution of 5-phenoxy-2-picoline in CH₂Cl₂ (70 mL) at room temperature was slowly added mCPBA (1.15 g) in portions over 1 h. Sodium metabisulfite was added to quench excess oxidant. The resulting suspension was filtered, treated with K₂CO₃, filtered again, then concentrated to afford crude 12 (390 mg, 31%), which was used in the next step without purification. ¹H NMR (CDCl₃) δ 8.05 (d, 1H, J=2.3 Hz), 7.43-7.35 (m, 2H), 7.24-7.19 (m, 1H), 7.17 (d, 1H, J=8.2 Hz), 7.07-7.02 (m, 2H), 6.89 (dd, 1H, J=8.7, 2.2 Hz), 2.48 (s, 3H).

(5-Phenoxypyridin-2-yl)methanol (13). A solution of 12 (390 mg, 1.90 mmol) in acetic anhydride (2.5 mL) and AcOH (1 mL) was heated to 150° C. for 5 min in a sealed tube. The resulting solution was concentrated then diluted with H₂O (5 mL) and CH₃OH (5 mL) K₂CO₃ (4.35 g) was added to adjust the solution to pH 8.5 and the mixture was extracted with EtOAc (3×25 mL). The combined EtOAc extracts were dried (Na₂SO₄) and concentrated to afford crude 13 (296 mg, 75% over two steps), which was used in the next step without purification. ¹H NMR (CDCl₃) δ 8.35 (d, 1H, J=1.9 Hz), 7.41-7.30 (m, 3H), 7.24 (d, 1H, J=8.5 Hz), 7.16 (t, 1H, J=7.4 Hz), 7.02 (d, 2H, J=7.7 Hz), 4.75 (s, 2H).

5-Phenoxypyridine-2-carboxylic Acid (14). Potassium permanganate (715 mg, 4.50 mmol) was added portion-wise over 2 h to a solution of 13 (296 mg, 1.50 mmol) in acetone (10 mL), keeping the temperature at 40-50° C. The resulting black suspension was filtered and retentate washed with 0.1 N aqueous NaOH. The resulting aqueous solution was corrected to pH 4 with 2 N aqueous HCl and extracted with CHCl₃ (3×25 mL). The combined CHCl₃ extracts were dried (Na₂SO₄) and concentrated to afford crude 14 (182 mg, 57%), which was used in the next step without purification. ¹H NMR (CDCl₃) δ 8.38 (d, 1H, J=2.5 Hz), 8.17 (d, 1H, J=8.6 Hz), 7.50-7.24 (m, 4H), 7.11 (d, 2H, J=7.6 Hz).

3-{(2S)-4-[(2S)-2-Amino-3-methylbutyl]-2-methylpiperazin-1-yl}phenol (17). To a mixture of 15 (3.54 g, 10.0 mmol), N-Boc-L-valine (2.39 g, 11.0 mmol) and Et₃N (4.17 mL, 30.0 mmol) in CH₃CN (50 mL) at room temperature was added a solution of HBTU (4.17 g, 11.0 mmol) in CH₃CN (50 mL). The reaction was stirred for 16 h. The mixture was poured into saturated NaHCO₃ (20 mL) and extracted with EtOAc (3×100 mL). The combined EtOAc extracts were washed with brine (100 mL), dried (Na₂SO₄) and concentrated. Flash column chromatography of the residue on silica gel using an EtOAc gradient in hexane gave the required amide 16 (3.70 g, 95%). The amide was then dissolved in THF (50 mL). To the solution was added 1 M solution of BH₃.THF (28.4 mL, 28.4 mmol) and the mixture was stirred at room temperature overnight. The reaction was carefully quenched by H₂O. Concentrated HCl (20 mL) was added and the mixture was refluxed for 2 h. The mixture was carefully basified to pH 8 with saturated NaHCO₃. The layers were separated and the aqueous layer was extracted with CH₂Cl₂ (3×100 mL). The combined organic phases were washed with brine (3×30 mL), dried (Na₂SO₄) and concentrated. Flash column chromatography of the crude product on silica gel using 0→40% 80CMA in CH₂Cl₂ afforded 17 (2.08 g, 79%) as a white solid: [α]$^{25}_D$ +44.4° (c 1.00, CH₃OH); ¹H NMR (CDCl₃) δ 7.09 (t, 1H, J=9.0 Hz), 6.52-6.45 (m, 1H), 6.40-6.30 (m, 2H), 3.92-3.84 (m, 1H), 3.22-3.10 (m, 2H), 2.78-2.70 (m, 3H), 2.56-2.45 (m, 2H), 2.38-2.27 (m, 3H), 1.68-1.58 (m, 1H), 1.08 (d, 3H, J=6.0 Hz), 0.96 (d, 3H, J=6.0 Hz), 0.94 (d, 3H, J=6.0 Hz); ¹³C NMR (CDCl₃) δ 158.2, 151.7, 129.9, 108.6, 107.2, 104.5, 62.2, 58.2, 55.0, 53.2, 51.2, 44.5, 31.9, 19.2, 18.8, 13.3; MS (ESI) m/z 278.6 (M+H)⁺.

6-Phenoxynicotinic Acid Methyl Ester (20). To a solution of 6-chloronicotinic acid (0.78 g, 5.00 mmol) in toluene (50 mL) and CH₃OH (10 mL) was slowly added a solution of trimethylsilyldiazomethane (2.75 mL, 2.0 M in ether). After stirring at room temperature for 30 min, AcOH (0.5 mL) was added, and the solution was concentrated to dryness to yield crude 6-chloronicotinic acid methyl ester. The crude ester was dissolved in CH₃CN (50 mL) and phenol (1.10 g, 11.0 mmol), Cs₂CO₃ (0.98 g), and K₂CO₃ (0.74 g) were then added. The mixture was refluxed overnight. The reaction showed incomplete conversion, so the solvent was replaced with DMF (10 mL), K₂CO₃ (0.91 g) and phenol (0.64 g) were added, and the mixture was refluxed for 1 h. The mixture was poured into ice and extracted with Et₂O (3×25 mL). The combined organic layers were washed with aqueous Na₂CO₃ and brine, dried (Na₂SO₄), and concentrated to yield crude 20.

6-Phenoxynicotinic Acid (21). A mixture of crude 20 and LiOH (0.49 g) in CH₃OH (15 mL) and H₂O (5 mL) was stirred at room temperature overnight. Following adjustment to pH 5 with 1 M NaHSO₄, extraction with EtOAc and concentration gave 21 (312 mg, 29% over three steps) as a white solid. ¹H NMR (CD₃OD) δ 8.72 (d, 1H, J=2.2 Hz), 8.34 (dd, 1H, J=8.7, 2.4 Hz), 7.48-7.41 (m, 2H), 7.27 (t, 1H, J=7.5 Hz), 7.15 (d, 2H, J=8.4 Hz), 7.00 (d, 1H, J=8.7 Hz).

N-(1S)-1-{[(3S)-4-(3-Hydroxyphenyl)-3-methylpiperazin-1-yl]methyl}-2-methylpropyl-4-phenoxybenzamide Dihydrochloride (6a). To a solution of 17 (55.5 mg, 0.20 mmol), 4-phenoxybenzoic acid (48.6 mg, 0.022 mmol) and Et₃N (0.056 mL, 0.40 mmol) in CH₃CN (10 mL) at room temperature was added HBTU (91.0 mg, 0.24 mmol). The reaction was stirred for 3 h. The mixture was diluted with Et₂O (50 mL), washed with saturated NaHCO₃ (2×10 mL), brine (2×10 mL), dried (Na₂SO₄) and concentrated. The crude product was purified by preparative TLC (33% 80CMA/CH₂Cl₂) to afford 6a free base (68.0 mg, 72%) as a glassy solid. ¹H NMR (CDCl₃) δ 7.76 (d, 2H, J=9.0 Hz), 7.36 (t, 2H, J=9.0 Hz), 7.14 (d, 1H, J=9.0 Hz), 7.10-6.90 (m, 5H), 6.50-6.30 (m, 4H), 4.30-4.22 (m, 1H), 3.80-3.65 (m, 1H), 3.20-2.94 (m, 2H), 2.82-2.70 (m, 2H), 2.68-2.52 (m, 1H), 2.50-2.30 (m, 3H), 2.11-1.94 (m, 1H), 0.99 (d, 3H, J=6.0 Hz), 0.97 (d, 3H, J=6.0 Hz), 0.88 (d, 3H, J=6.0 Hz); ¹³C NMR (CDCl₃) δ 167.5, 160.4, 157.5, 155.9, 151.3, 130.0, 129.8, 129.1, 128.9, 124.2, 119.8, 117.8, 108.5, 106.8, 103.9, 58.5, 57.9, 54.4, 51.4, 50.9, 43.8, 30.9, 18.9, 18.1, 12.8; MS (ESI) m/z 474.7 (M+H)⁺. The free base was converted to the dihydrochloride salt as an off-white solid: mp 135° C. (fusion); [α]²⁵_D +77.5° (c 0.50, CH₃OH); Anal. (C₂₉H₃₇Cl₂N₃O₃) C, H, N.

N-(1S)-1-{[(3S)-4-(3-Hydroxyphenyl)-3-methylpiperazin-1-yl]methyl}-2-methylpropyl-4-(4-methylphenoxy) benzamide Dihydrochloride (6b). General procedure B using acid 10a afforded 6b (11.8 mg, 48%) as a white solid: mp 160° C. (fusion); [α]²⁵_D +60.6° (c 0.33, CH₃OH); Anal. (C₃₀H₃₉Cl₂N₃O₃.1.5H₂O) C, H, N. 6b free base: ¹H NMR (CDCl₃) δ 7.74 (d, 2H, J=8.7 Hz), 6.42-6.27 (m, 3H), 7.04 (t, 1H, J=8.1 Hz), 6.94 (d, 2H, J=8.7 Hz), 6.92 (d, 2H, J=8.4 Hz), 4.28-4.17 (m, 1H), 3.85-3.71 (m, 1H), 3.21-2.97 (m, 2H), 2.85-2.73 (m, 2H), 2.65-2.53 (m, 1H), 2.46-2.30 (m, 3H), 2.34 (s, 3H), 2.14-2.02 (m, 1H), 0.99 (d, 3H, J=6.7 Hz), 0.97 (d, 3H, J=6.8 Hz), 0.89 (d, 3H, J=6.7 Hz); ¹³C NMR (CDCl₃) δ 167.3, 160.9, 157.1, 153.5, 151.4, 133.9, 130.4, 129.9, 129.0, 128.7, 119.8, 117.3, 108.5, 106.3, 103.4, 58.6, 57.9, 54.5, 51.3, 50.9, 43.6, 31.6, 30.8, 22.6, 20.7, 18.9, 18.0, 14.1, 12.7; MS (ESI) m/z 488.6 (M+H)⁺.

N-(1S)-1-{[(3S)-4-(3-Hydroxyphenyl)-3-methylpiperazin-1-yl]methyl}-2-methylpropyl-4-(3-fluorophenoxy) benzamide Dihydrochloride (6c). General procedure B using acid 10b afforded 6c (14.4 mg, 51%) as a white solid: mp 85° C. (fusion); [α]²⁵_D +61.3° (c 0.46, CH₃OH). Anal. (C₂₉H₃₆Cl₂FN₃O₃.2H₂O) C, H, N. 6c free base: ¹H NMR (CDCl₃) δ 7.81 (d, 2H, J=8.8 Hz), 7.32-7.21 (m, 1H), 7.00 (t, 1H, J=8.1 Hz), 6.93 (d, 2H, J=8.6 Hz), 6.87-6.65 (m, 3H), 6.40 (s, 1H), 6.39 (d, 1H, J=7.2 Hz), 6.30 (d, 1H, J=8.0 Hz), 4.39-4.26 (m, 1H), 3.81-3.70 (m, 1H), 3.19-2.93 (m, 3H), 2.93-2.80 (m, 2H), 2.74-2.46 (m, 3H), 2.09-1.94 (m, 1H), 1.00 (d, 6H, J=6.8 Hz), 0.90 (d, 3H, J=6.5 Hz); ¹³C NMR (CDCl₃) δ 167.3, 165.1, 161.9, 159.4, 157.3, 151.1, 131.6, 130.7, 130.6, 129.9, 129.7, 129.1, 118.3, 117.9, 114.8, 114.8, 111.0, 110.7, 110.4, 109.9, 107.7, 107.2, 106.9, 104.9, 58.3, 57.9, 53.8, 50.9, 50.7, 31.2, 19.0, 18.1, 13.4; MS (ESI) m/z 492.4 (M+H)⁺.

N-(1S)-1-{[(3S)-4-(3-Hydroxyphenyl)-3-methylpiperazin-1-yl]methyl}-2-methylpropyl-4-(3-methylphenoxy) benzamide Dihydrochloride (6d). General procedure B using acid 10c afforded 6d (17.8 mg, 32%) as a white solid: mp 165° C. (fusion); [α]²⁵_D +63.8° (c 0.58, CH₃OH); Anal. (C₃₀H₃₉Cl₂N₃O₃.1.5H₂O) C, H, N. 6d free base: ¹H NMR (CDCl₃) δ 7.77 (d, 2H, J=8.6 Hz), 7.22 (t, 1H, J=7.8 Hz), 7.05-6.75 (m, 5H), 6.91 (d, 2H, J=8.7 Hz), 6.41-6.35 (m, 2H), 6.32 (d, 1H, J=8 Hz), 4.34-4.20 (m, 1H), 3.81-3.70 (m, 3H), 3.18-2.96 (m, 2H), 2.91-2.76 (m, 2H), 2.65-2.41 (m, 3H), 2.31 (s, 3H), 2.09-1.95 (m, 1H), 1.00 (d, 3H, J=6.8 Hz), 0.99 (d, 3H, J=6.8 Hz), 0.89 (d, 3H, J=6.7 Hz); ¹³C NMR (CDCl₃) δ 167.4, 160.5, 157.3, 155.9, 151.2, 140.2, 131.5, 129.9, 129.6, 129.5, 128.9, 128.8, 125.0, 124.7, 120.4, 120.4, 117.7, 117.2, 116.7, 116.7, 109.4, 107.2, 104.5, 58.4, 57.9, 54.0, 50.9, 31.5, 31.1, 29.0, 25.3, 22.6, 21.3, 19.0, 18.1, 14.1, 13.2; MS (ESI) m/z 488.6 (M+H)⁺.

N-(1S)-1-{[(3S)-4-(3-Hydroxyphenyl)-3-methylpiperazin-1-yl]methyl}-2-methylpropyl-4-(2-methoxyphenoxy) benzamide Dihydrochloride (6e). General procedure B using acid 10d afforded 6e (24.0 mg, 83%) as a white solid: mp 145° C. (fusion); [α]²⁵_D +57.8° (c 0.86, CH₃OH). Anal. (C₃₀H₃₉Cl₂N₃O₄.2.5H₂O) C, H, N. 6e free base: ¹H NMR (CDCl₃) δ 7.76 (d, 2H, J=8.8 Hz), 7.21-7.12 (m, 1H), 7.06-6.88 (m, 4H), 6.84 (d, 2H, J=8.8 Hz), 6.39 (s, 1H), 6.38 (d, 1H, J=7.5 Hz), 6.30 (d, 1H, J=7.8 Hz), 4.37-4.23 (m, 1H), 3.82-3.69 (m, 1H), 3.74 (s, 3H), 3.20-2.82 (m, 5H), 2.74-2.47 (m, 3H), 2.07-1.93 (m, 1H), 0.99 (d, 6H, J=6.9 Hz), 0.88 (d, 3H, J=6.4 Hz); ¹³C NMR (CDCl₃) δ 167.6, 161.0, 157.4, 151.7, 151.1, 143.7, 131.5, 129.9, 128.8, 128.1, 125.8, 125.6, 122.1, 121.2, 121.3, 121.2, 116.1, 115.8, 113.0, 109.7, 107.6, 104.8, 64.4, 58.4, 57.9, 55.9, 55.9, 53.9, 50.9, 50.7, 44.3, 31.6, 31.2, 30.6, 22.6, 19.1, 19.0, 18.1, 13.7, 13.2; MS (ESI) m/z 504.6 (M+H)⁺.

N-(1S)-1-{[(3S)-4-(3-Hydroxyphenyl)-3-methylpiperazin-1-yl]methyl}-2-methylpropyl-4-(3-methoxyphenoxy) benzamide Dihydrochloride (6f). General procedure B using acid 10e afforded 6f (11.3 mg, 55%) as a beige solid: mp 145° C. (fusion); [α]²⁵_D +57.6° (c 0.59, CH₃OH); Anal. (C₃₀H₃₉Cl₂N₃O₄.2H₂O) C, H, N. (6f). free base: ¹H NMR (CDCl₃) δ 7.77 (d, 2H, J=8.7 Hz), 7.25 (t, 1H, J=7.9 Hz), 7.05 (t, 1H, J=8.0 Hz), 7.01 (d, 2H, J=8.8 Hz), 6.74-6.56 (m, 3H), 6.43-6.28 (m, 3H), 4.27-4.15 (m, 1H), 3.85-3.74 (m, 1H), 3.77 (s, 3H), 3.23-3.11 (m, 1H), 3.11-2.98 (m, 1H), 2.84-2.71 (m, 2H), 2.66-2.54 (m, 1H), 2.51-2.30 (m, 3H), 2.11-1.94 (m, 1H), 0.99 (d, 2H, J=6.7 Hz), 0.98 (d, 2H, J=6.7 Hz), 0.89 (d, 2H, J=6.5 Hz); $^{13}$C NMR (CDCl$_3$) δ 167.3, 161.1, 160.1, 157.3, 157.0, 151.4, 130.4, 129.9, 129.5, 128.8, 128.7, 118.1, 118.0, 111.7, 109.9, 108.6, 106.2, 106.2, 105.7, 103.3, 58.6, 57.8, 55.4, 54.5, 51.3, 50.9, 43.5, 30.8, 18.9, 18.0, 12.8; MS (ESI) m/z 504.5 (M+H)$^+$.

N-(1S)-1-{[(3S)-4-(3-Hydroxyphenyl)-3-methylpiperazin-1-yl]methyl}-2-methylpropyl-4-(4-hydroxyphenoxy)benzamide Dihydrochloride (6g). General procedure C using acid 10h afforded 6g (33.8 mg, 48%) as a white solid: mp 185° C. (fusion); [α]$^{25}_D$ +62.4° (c 1.60, CH$_3$OH). Anal. (C$_{29}$H$_{37}$Cl$_2$N$_3$O$_4$.1.5H$_2$O) C, H, N. 6g free base: $^1$H NMR (CD$_3$OD) δ 7.81 (d, 2H, J=8.8 Hz), 7.03 (t, 1H, J=8.1 Hz), 6.95-6.87 (m, 4H), 6.85-6.79 (m, 2H), 6.46-6.26 (m, 3H), 4.26-4.16 (m, 1H), 3.85-3.72 (m, 1H), 3.18-2.93 (m, 3H), 2.90-2.78 (m, 3H), 2.76-2.62 (m, 1H), 2.58-2.40 (m, 3H), 1.98-1.93 (m, 1H), 3.54 (d, 3H, J=7.1 Hz), 1.00 (d, 3H, J=7.0 Hz), 0.92 (d, 3H, J=6.6 Hz); $^{13}$C NMR (CD$_3$OD) δ 170.0, 163.3, 159.3, 155.7, 152.9, 149.3, 130.8, 130.3, 122.7, 117.4, 117.3, 110.3, 108.3, 105.7, 60.8, 59.2, 55.3, 53.0, 52.8, 46.1, 46.1, 33.0, 32.8, 23.7, 20.1, 18.8, 14.5, 13.5; MS (ESI) m/z 490.7 (M+H)$^+$.

N-(1S)-1-{[(3S)-4-(3-Hydroxyphenyl)-3-methylpiperazin-1-yl]methyl}-2-methylpropyl-4-(2-hydroxyphenoxy)benzamide Dihydrochloride (6h). General procedure C using acid 10i afforded 6h (31.5 mg, 44%) as a white solid: mp 173° C. (fusion); [α]$^{25}_D$ +60.0° (c 1.50, CH$_3$OH). Anal. (C$_{29}$H$_{37}$Cl$_2$N$_3$O$_4$.CH$_3$OH) C, H, N. 6h free base: $^1$H NMR (CD$_3$OD) δ 7.8 (d, 2H, J=8.8 Hz), 7.13-6.81 (m, 7H), 6.45-6.26 (m, 3H), 4.26-4.15 (m, 1H), 3.85-3.71 (m, 1H), 3.18-2.94 (m, 3H), 2.91-2.79 (m, 3H), 2.77-2.63 (m, 1H), 2.58-2.39 (m, 3H), 1.96-1.82 (m, 1H), 1.02 (d, 3H, J=7.0 Hz), 0.99 (d, 3H, J=6.9 Hz), 0.92 (d, 3H, J=6.4 Hz); $^{13}$C NMR (CD$_3$OD) δ 170.0, 162.5, 159.3, 152.9, 150.7, 143.8, 140.0, 130.8, 130.2, 129.8, 127.1, 123.2, 121.3, 118.5, 117.0, 110.3, 108.3, 105.7, 101.4, 60.8, 59.2, 55.3, 53.0, 52.8, 46.0, 32.8, 20.1, 18.8, 13.5; MS (ESI) m/z 490.7 (M+H)$^+$.

N-(1S)-1-{[(3S)-4-(3-Hydroxyphenyl)-3-methylpiperazin-1-yl]methyl}-2-methylpropyl-4-(3-hydroxyphenoxy)benzamide Dihydrochloride (6i). General procedure C using acid 10j afforded 6i (23.7 mg, 33%) as a white solid: mp 132° C. (fusion); [α]$^{25}_D$ +59.6° (c 1.51, CH$_3$OH); Anal. (C$_{29}$H$_{37}$Cl$_2$N$_3$O$_4$.2H$_2$O) C, H, N. 6i free base: $^1$H NMR (CD$_3$OD) δ 7.85 (d, 2H, J=8.7 Hz), 7.18 (t, 1H, J=8.0 Hz), 7.07-6.97 (m, 3H), 6.65-6.59 (m, 1H), 6.53-6.37 (m, 4H), 6.34-6.29 (m, 1H), 4.28-4.17 (m, 1H), 3.85-3.74 (m, 1H), 3.19-2.94 (m, 3H), 2.93-2.66 (m, 4H), 2.63-2.42 (m, 3H), 1.98-1.84 (m, 1H), 1.02 (d, 3H, J=6.8 Hz), 1.00 (d, 3H, J=6.9 Hz), 0.93 (d, 3H, J=6.4 Hz); $^{13}$C NMR (CD$_3$OD) δ 169.9, 161.9, 160.3, 159.3, 158.5, 152.8, 131.6, 130.9, 130.5, 130.4, 118.7, 112.5, 111.7, 110.4, 108.4, 108.0, 105.8, 104.6, 98.2, 60.8, 59.2, 55.3, 53.0, 52.7, 32.8, 20.1, 18.8, 13.6; MS (ESI) m/z 490.7 (M+H)$^+$.

N-(1S)-1-{[(3S)-4-(3-Hydroxyphenyl)-3-methylpiperazin-1-yl]methyl}-2-methylpropyl-4-(4-methoxyphenoxy)benzamide Dihydrochloride (6j). General procedure C using acid 10f afforded 6j (27.6 mg, 39%) as a white solid: mp 125° C. (fusion); [α]$^{25}_D$ +64.5° (c 1.01, CH$_3$OH). Anal. (C$_{30}$H$_{39}$Cl$_2$N$_3$O$_4$.H$_2$O) C, H, N. 6j free base: $^1$H NMR (CDCl$_3$) δ 7.74 (d, 2H, J=8.8 Hz), 7.08-6.84 (m, 7H), 6.48 (br s, 1H), 6.41-6.24 (m, 3H), 4.30-4.17 (m, 1H), 3.81-3.70 (m, 1H), 3.80 (s, 3H), 3.19-2.93 (m, 2H), 2.86-2.56 (m, 4H), 2.54-2.30 (m, 3H), 2.10-1.94 (m, 1H), 1.01-0.93 (m, 6H), 0.87 (d, 3H, J=6.4 Hz); $^{13}$C NMR (CDCl$_3$) δ 167.4, 161.4, 157.2, 156.5, 151.3, 149.0, 129.9, 128.8, 121.4, 116.7, 115.0, 108.9, 106.7, 103.8, 58.44, 57.9, 57.8, 55.7, 54.3, 51.1, 50.9, 43.8, 43.8, 30.9, 18.9, 18.0, 12.9; MS (ESI) m/z 504.7 (M+H)$^+$.

N-(1S)-1-{[(3S)-4-(3-Hydroxyphenyl)-3-methylpiperazin-1-yl]methyl}-2-methylpropyl-3-methyl-4-phenoxybenzamide Dihydrochloride (6k). General procedure C using acid 10g afforded 6k (31.9 mg, 45%) as a pale yellow solid: mp 88° C. (fusion); [α]$^{25}_D$ +62.1° (c 1.51, CH$_3$OH). Anal. (C$_{30}$H$_{39}$Cl$_2$N$_3$O$_3$.H$_2$O) C, H, N. 6k free base: $^1$H NMR (CDCl$_3$) δ 7.70 (s, 1H), 7.56 (d, 1H, J=8.5 Hz), 7.32 (t, 2H, J=8.3 Hz), 7.09 (t, 1H, J=7.5 Hz), 7.03 (t, 1H, J=7.9 Hz), 6.92 (d, 2H, J=8.1 Hz), 6.81 (d, 1H, J=8.4 Hz), 6.46 (br s, 1H), 6.41-6.28 (m, 3H), 4.32-4.17 (m, 1H), 3.83-3.69 (m, 1H), 3.18-2.95 (m, 2H), 2.86-2.58 (m, 3H), 2.52-2.32 (m, 3H), 2.27 (s, 3H), 2.10-1.96 (m, 1H), 1.02-0.93 (m, 6H), 0.89 (d, 3H, J=6.4 Hz); $^{13}$C NMR (CDCl$_3$) δ 167.6, 157.9, 157.3, 151.3, 130.3, 129.9, 129.7, 129.7, 129.5, 126.0, 123.4, 118.4, 118.1, 108.7, 106.8, 103.9, 103.2, 96.8, 58.5, 57.9, 54.3, 51.2, 50.9, 30.9, 18.9, 18.0, 16.2, 12.9; MS (ESI) m/z 488.6 (M+H)$^+$.

3-Chloro-N-[(2S)-1-[(3S)-4-(3-hydroxyphenyl)-3-methylpiperazin-1-yl]-3-methylbutan-2-yl]-4-(3-methylphenoxy)benzamide Dihydrochloride (6l). General procedure C using acid 10k afforded 6l (25 mg, 41%) as a white solid: mp 154-158° C. (fusion), [α]$^{25}_D$ +63.2° (c 0.95, CH$_3$OH). Anal. (C$_{30}$H$_{38}$Cl$_3$N$_3$O$_3$—H$_2$O) C, H, N. 6l free base: $^1$H NMR (CDCl$_3$) δ 7.87 (s, 1H), 7.60 (d, 1H, J=8.5 Hz), 7.23 (t, 1H, J=7.7 Hz), 7.04 (t, 1H, J=8.0 Hz), 6.97 (d, 1H, J=7.4 Hz), 6.88 (d, 1H, J=8.5 Hz), 6.84-6.76 (m, 2H), 6.40 (d, 1H, J=8.2 Hz), 6.35-6.25 (m, 3H), 4.26-4.12 (m, 1H), 3.85-3.74 (m, 1H), 3.17 (d, 1H, J=11.7 Hz), 3.04 (t, 1H, J=10.0 Hz), 2.77 (t, 2H, J=8.8 Hz), 2.64-2.52 (m, 1H), 2.48-2.29 (m, 3H), 2.33 (s, 3H), 2.11-1.97 (m, 1H), 1.05-0.93 (m, 6H), 0.89 (d, 3H, J=6.4 Hz); $^{13}$C NMR (CDCl$_3$) δ 166.2, 157.0, 155.7, 151.4, 140.3, 130.7, 129.9, 129.7, 129.5, 126.7, 125.2, 125.1, 119.7, 119.0, 116.0, 108.6, 106.3, 103.4, 58.5, 57.9, 54.5, 51.5, 50.9, 43.6, 30.8, 21.4, 18.9, 18.1, 12.8; MS (ESI) m/z 522.4 (M+H)$^+$.

4-(2-Hydroxy-5-methylphenoxy)-N-[(2S)-1-[(3S)-4-(3-hydroxyphenyl)-3-methylpiperazin-1-yl]-3-methylbutan-2-yl]benzamide Dihydrochloride (6m). General procedure C using acid 10m afforded 6m (43 mg, 72%) as a white solid: mp 179-183° C. (fusion); [α]$^{25}_D$ +56.5° (c 1.35, CH$_3$OH). Anal. (C$_{30}$H$_{39}$Cl$_2$N$_3$O$_4$.H$_2$O) C, H, N. 6m free base: $^1$H NMR (CDCl$_3$) δ 7.70 (d, 2H, J=8.8 Hz), 7.01 (t, 1H, J=8.1 Hz), 6.96-6.82 (m, 4H), 6.72 (s, 1H), 6.41-6.26 (m, 4H), 4.27-4.14 (m, 1H), 3.70-3.58 (m, 1H), 3.06 (d, 1H, J=11.7 Hz), 2.95 (t, 1H, J=10.5 Hz), 2.71 (d, 2H, J=10.6 Hz), 2.56 (t, 1H, J=11.3 Hz), 2.45-2.18 (m, 3H), 2.21 (s, 3H), 2.07-1.93 (m, 1H), 1.00-0.91 (m, 6H), 0.81 (d, 3H, J=6.4 Hz); $^{13}$C NMR (CDCl$_3$) δ 167.5, 160.2, 157.2, 151.4, 145.7, 142.1, 130.5, 129.9, 129.2, 128.8, 128.8, 126.2, 120.9, 116.9, 116.7, 108.8, 106.7, 103.8, 58.6, 57.9, 54.4, 51.4, 51.0, 43.9, 30.9, 20.6, 18.9, 18.0, 12.9; MS (ESI) m/z 504.6 (M+H)$^+$.

N-(1S)-1-{[(3S)-4-(3-Hydroxyphenyl)-3-methylpiperazin-1-yl]methyl}-2-methylpropyl]-5-phenoxypyridine-2-carboxamide Trihydrochloride (7a). To a solution of 14 (182 mg, 0.85 mmol) in CH$_3$CN (10 mL) at room temperature were added HBTU (355 mg, 0.94 mmol), Et$_3$N (0.24 mL, 1.7 mmol), and 17 (230 mg, 0.85 mmol). THF (2 mL) was added for solubility. The reaction mixture was stirred for 12 h and concentrated. Flash column chromatography of the crude product on silica gel using an EtOAc gradient in hexane afforded 7a free base: $^1$H NMR (CDCl$_3$) δ 8.29 (d, 1H, J=2.6 Hz), 8.13 (d, 1H, J=8.7 Hz), 7.94 (d, 1H, J=9.0 Hz), 7.45-7.36 (m, 2H), 7.32 (dd, 1H, J=8.6, 2.9 Hz), 7.21

(t, 1H, J=7.3 Hz), 7.11-7.03 (m, 3H), 6.43 (dd, 1H, J=8.2, 1.6 Hz), 6.32 (s, 1H), 6.25 (d, 1H, J=7.2 Hz), 4.67 (br s, 1H), 4.26-4.12 (m, 1H), 3.92-3.78 (m, 1H), 3.27-3.14 (m, 1H), 3.06 (td, 1H, J=11.4, 3.3 Hz), 2.89 (d, 1H, J=11.4 Hz), 2.78 (d, 1H, J=11.0 Hz), 2.62-2.52 (m, 1H), 2.48-2.28 (m, 3H), 2.15-1.95 (m, 1H), 1.01 (d, 3H, J=4.7 Hz), 0.98 (d, 3H, J=4.7 Hz), 0.93 (d, 3H, J=6.3 Hz); $^{13}$C NMR (CDCl$_3$) δ 164.1, 157.7, 156.5, 155.2, 151.4, 144.3, 138.8, 130.2, 129.7, 124.9, 124.9, 123.5, 119.7, 108.0, 106.3, 103.5, 59.3, 58.2, 54.3, 51.4, 50.9, 43.5, 30.7, 19.3, 17.7, 12.6. MS (ESI) m/z 476.0 (M+H)$^+$. The free base was converted to the trihydrochloride salt (121 mg, 31%) as a tan solid: mp 95° C. (fusion); [α]$^{25}_D$ +73.1° (c 0.67, CH$_3$OH). Anal. (C$_{28}$H$_{37}$Cl$_3$N$_4$O$_3$.0.5 EtOAc) C, H, N.

N-[(2S)-1-[(3S)-4-(3-Hydroxyphenyl)-3-methylpiperazin-1-yl]-3-methylbutan-2-yl]-6-phenoxypyridine-3-carboxamide Trihydrochloride (7b). General procedure C using acid 21 afforded 7b (33 mg, 51%) as a white solid: mp 168-170° C. (fusion), [α]$^{25}_D$ +59.7° (c 1.55, CH$_3$OH). Anal. (C$_{29}$H$_{39}$Cl$_3$N$_4$O$_3$.2.5H$_2$O) C, H, N. 7b free base: $^1$H NMR (CDCl$_3$) δ 8.57 (d, 1H, J=2.3 Hz), 8.12 (dd, 1H, J=8.6, 2.5 Hz), 7.41 (t, 2H, J=7.9 Hz), 7.23 (t, 1H, J=7.4 Hz), 7.16-7.10 (m, 2H), 7.04 (t, 1H, J=8.0 Hz), 6.91 (d, 1H, J=8.6 Hz), 6.38 (d, 1H, J=8.0 Hz), 6.33-6.23 (m, 3H), 4.27-4.12 (m, 1H), 3.83-3.71 (m, 1H), 3.19-3.09 (m, 1H), 3.06-2.95 (m, 1H), 2.75 (d, 2H, J=10.8 Hz), 2.62-2.49 (m, 1H), 2.46-2.25 (m, 3H), 2.11-1.96 (m, 1H), 1.01-0.93 (m, 6H), 0.86 (d, 3H, J=6.4 Hz); $^{13}$C NMR (CDCl$_3$) δ 165.7, 165.6, 157.1, 153.5, 151.4, 146.4, 139.0, 129.9, 129.8, 125.8, 125.3, 121.4, 111.1, 108.6, 106.4, 103.5, 58.5, 57.8, 54.5, 51.4, 50.9, 43.6, 30.7, 18.8, 18.0, 12.8; MS (ESI) m/z 475.7 (M+H)$^+$.

General Procedure D.[1] The appropriate phenol (1.4 mmol) and KOH (1.1 mmol) were dissolved in DMF (1.5 mL) before the appropriate 4-fluorobenzaldehyde (1 mmol) was added. The solution was heated in a sealed tube to 175° C. for 20 min, poured into H$_2$O (25 mL) and extracted with Et$_2$O (75 mL). The organic layer was washed with H$_2$O (25 mL), brine (10 mL) and dried (Na$_2$SO$_4$). The crude residue was dissolved in 5:1 acetonitrile:water (6 mL) along with NaH$_2$PO$_4$ (36 mg) and H$_2$O$_2$ (150 μL, 30%). In an ice bath, a solution of NaClO$_2$ (158 mg) in water (1.5 mL) is slowly added. After 12 h at r.t., the reaction was quenched with Na$_2$S$_2$O$_3$, diluted with brine and extracted with EtOAc. The desired benzoic acid was isolated by extracting into aqueous base, acidification, and extraction into EtOAc.

4-(2-Fluorophenoxy)benzoic Acid (18a) was prepared by heating a mixture of KOH (219 mg, 3.3 mmol), 2-fluorophenol (310 μL, 3.5 mmol), and 4-fluorobenzonitrile (377 mg, 3.1 mmol) in DMF (1.5 mL) to 175° C. for 20 min in a sealed tube. Ether extraction gave the intermediate crude diaryl ether. Refluxing in 30% KOH aq. resulted in incomplete hydrolysis of the nitrile, so the material was refluxed in 50% aq. H$_2$SO$_4$ (10 mL) and AcOH (5 ml). Silica chromatography (gradient 5-100% EtOAc in hexanes) gave the desired acid (18a) (405 mg, 56%). $^1$H NMR (CDCl$_3$) δ 8.07 (d, 2H, J=8.9 Hz), 7.29-7.13 (m, 4H), 6.99 (d, 2H, J=8.8 Hz); MS (ESI) m/z 231.6 (M–H)$^-$.

4-(3-(Trifluoromethyl)phenoxy)benzoic Acid (18b) was prepared by heating a mixture of KOH (203 mg, 3.0 mmol), 3-(trifluoromethyl)phenol (389 μL, 3.2 mmol), and 4-fluorobenzonitrile (348 mg, 2.9 mmol) in DMF (1.5 mL) to 175° C. for 20 min in a sealed tube. Ether extraction gave the intermediate crude diaryl ether. Refluxing in 30% KOH aq. resulted in incomplete hydrolysis of the nitrile, so the material was refluxed in 50% aq. H$_2$SO$_4$ (10 mL) and AcOH (5 ml). Silica chromatography (gradient 5-100% EtOAc in hexanes) gave the desired acid (18b) (190 mg, 23%). $^1$H NMR (CDCl$_3$) δ 8.11 (d, 2H, J=8.9 Hz), 7.56-7.43 (m, 2H), 7.34 (s, 1H), 7.15 (t, 1H, J=8.6 Hz), 7.05 (d, 2H, J=8.8 Hz); MS (ESI) m/z 281.4 (M–H)$^-$.

4-(3-Chlorophenoxy)benzoic Acid (18c) was prepared by heating a mixture of KOH (199 mg, 3.0 mmol), 3-chlorophenol (337 μL, 3.2 mmol), and 4-fluorobenzonitrile (348 mg, 2.9 mmol) in DMF (1.5 mL) to 175° C. for 20 min in a sealed tube. Ether extraction gave the intermediate crude diaryl ether, which was refluxed 12 h in 30% KOH aq. The resulting solution was extracted with EtOAc, acidified, then extracted to yield the desired acid (18c) (766 mg, 99+%). $^1$H NMR (CDCl$_3$) δ 8.10 (d, 2H, J=8.7 Hz), 7.32 (t, 1H, J=8.1 Hz), 7.21-7.16 (m, 1H), 7.08 (t, 1H, J=2.0 Hz), 7.04 (d, 2H, J=8.8 Hz), 7.00-6.95 (m, 1H); MS (ESI) m/z 247.3 (M–H)$^-$.

4-(3-Bromophenoxy)benzoic Acid (18d) was prepared by heating a mixture of KOH (220 mg, 3.3 mmol), 3-bromophenol (605 mg, 3.5 mmol), and 4-fluorobenzonitrile (377 mg, 3.1 mmol) in DMF (1.5 mL) to 175° C. for 20 min in a sealed tube. Ether extraction gave the intermediate crude diaryl ether. Refluxing in 30% KOH aq. resulted in incomplete hydrolysis of the nitrile, so the material was refluxed in 50% aq. H$_2$SO$_4$ (10 mL) and AcOH (5 ml). Silica chromatography (gradient 5-100% EtOAc in hexanes) gave the desired acid (18d) (371 mg, 61%). $^1$H NMR (CDCl$_3$) δ 8.10 (d, 2H, J=8.7 Hz), 7.37-7.21 (m, 3H), 7.07-6.99 (m, 3H); MS (ESI) m/z 291.1 (M–H)$^-$.

4-(2-hydroxy-3-methylphenoxy)benzoic Acid (18e) was prepared by heating a solution of 4-fluorobenzonitrile (1 mmol), 3-methylcatechol (1.1 mmol), and Cs$_2$CO$_3$ (1.1 mmol) in CH$_3$CN (2 mL) to 100° C. in a sealed tube for 5 min, then again to 125° C. to an additional 5 min. The resulting mixture was concentrated, dissolved in 30% KOH aq. and refluxed. When TLC analysis indicated hydrolysis was complete, the solution was acidified with 50% H$_2$SO$_4$ and extracted with EtOAc. Silica gel chromatography (gradient up to 100% EtOAc in hexanes) gave 18e (50 mg, 20%). $^1$H NMR (CDCl$_3$) δ 7.98 d, 2H, J=8.8 Hz), 7.10-6.95 (m, 2H), 6.89 (d, 2H, J=8.8 Hz), 6.82-6.75 (m, 1H), 2.08 (s, 3H); MS (ESI) m/z 243.3 (M–H)$^-$.

4-(3,5-dimethylphenoxy)benzoic Acid (18f) was prepared by heating a mixture of KOH (189 mg, 2.9 mmol), 3,5-dimethylphenol (380 mg, 3.1 mmol), and 4-fluorobenzonitrile (333 mg, 2.7 mmol) in DMF (2 mL) to 175° C. in a sealed tube for 20 min. The crude material from ether extraction was refluxed in 50% H$_2$SO$_4$ (10 mL) and AcOH (5 mL) for 12 h. The product was extracted with EtOAc (3×25 mL), washed with water then brine, dried with Na$_2$SO$_4$ and concentrated to yield 18f (641 mg, 96%). $^1$H NMR (CDCl$_3$) δ 8.06 (d, 2H, J=9.0 Hz), 6.99 (d, 2H, J=9.0 Hz), 6.84 (s, 1H), 6.70 (s, 2H), 2.32 (s, 3H).

3-Methyl-4-(3-methylphenoxy)benzoic Acid (18g) was prepared according to General Procedure A. Yield 28%. $^1$H NMR (CDCl$_3$) δ 8.01 (s, 1H), 7.88 (d, 1H, J=8.4 Hz), 7.24 (t, 1H, J=8.1 Hz), 6.97 (d, 1H, J=7.4 Hz), 6.86-6.77 (m, 3H), 2.35 (s, 3H), 2.34 (s, 3H).

3-Methoxy-4-(3-methylphenoxy)benzoic Acid (18h). Methyl 4-hydroxy-3-methyoxybenzoate was prepared in quantitative yield by Fischer esterification of the corresponding benzoic acid (3.04 g, 18.1 mmol) refluxed 12 h in methanol (50 mL) with catalytic dry HCl (2 mL, 2 M in ether). The phenol (546.6 mg, 3 mmol) was combined with 3-iodotoluene (654 mg, 1.0 eq) and Cu$_2$O (515 mg, 1.2 eq) in collidine (1 mL). The mixture was heated to 200° C. for 1 h in a sealed tube. The resulting solution was extracted with ether and washed with 2 N HCl. Silica gel (up to 50% EtOAc in hexanes) gave the desired intermediate ether (435 mg, 53%). The methyl ester was saponified with LiOH (3 eq) in dioxane/water (1:1, 9.6 mL) at r.t. The resulting solution was acidified with 2 N $H_2SO_4$, concentrated, filtered and washed with water to give 18h (355 mg, 46%). $^1H$ NMR (CDCl$_3$) δ, 3.96 (s, 3H).

3-Hydroxy-4-(3-methylphenoxy)benzoic Acid (18i) was prepared from 18h by refluxing in 48% HBr (4 mL) and AcOH (4 mL) for 4 h. Extraction with CH$_2$Cl$_2$, followed by concentration from toluene afforded 18i (99+%). $^1H$ NMR (CDCl$_3$) δ 7.77 (d, 1H, J=2.0 Hz), 7.59 (dd 1H, J=8.5, 2.1 Hz), 7.26 (t, 1H, J=7.9 Hz), 6.99 (d, 1H, J=7.3 Hz), 6.88 (s, 1H), 6.87-6.84 (m, 1H), 6.82 (d, 1H, J=8.5 Hz), 2.35 (s, 3H).

2-Chloro-4-(3-methylphenoxy)benzoic Acid (18j) was prepared from m-cresol (1.5 mmol), KOH (1.1 mmol) and 4-fluoro-2-methylbenzonitrile (1 mmol) in DMF (1.5 mL) heated to 175° C. for 20 min. The crude phenoxybenzonitrile from ether extraction was converted to the benzamide with NaOH in 50% ethylene glycol with careful addition of $H_2O_2$ (1.5 mL, 50%). The residue from EtOAc extraction was then dissolved in CH$_3$CN (7.5 mL) to which chilled 70% sulfuric acid was added (37 mL). The flask was wrapped with foil and NaNO$_2$ (0.6 g) was added in portions over 1 h. After 4 h, the solution was poured onto ice and filtered to yield 18j (134 mg, 55% over 3 steps). $^1H$ NMR (CD$_3$OD) δ 7.93 (d, 1H, J=8.6 Hz), 7.27 (t, 1H, J=7.8 Hz), 7.02 (d, 1H, J=7.7 Hz), 6.89-6.73 (m, 4H), 2.54 (s, 3H), 2.34 (s, 3H).

2-Methoxy-4-(3-methylphenoxy)benzoic Acid (18k) was prepared by heating a mixture of m-cresol (0.64 mL, 6.1 mmol), KOH (386 mg, 5.8 mmol), and 4-fluoro-2-methoxybenzonitrile (830 mg, 5.5 mmol) in DMF (2 mL) to 175° C. for 20 min. The resulting solution was extracted with ether, washed with water and dried (Na$_2$SO$_4$) to yield the crude intermediate phenoxybenzonitrile, which was refluxed in 30% KOH for 12 h. Following acidification and extraction with EtOAc, the residue was purified by silica gel (EtOAc gradient in hexanes) to yield 18k (415 mg, 29% over 2 steps). $^1H$ NMR (CDCl$_3$) δ 8.10 (d, 1H, J=8.8 Hz), 7.30 (t, 1H, J=8.2 Hz), 7.05 (d, 1H, J=7.7 Hz), 6.93-6.84 (m, 2H), 6.66 (d, 1H, J=2.1 Hz), 6.60 (dd, 1H, J=8.7, 2.2 Hz), 4.00 (s, 3H), 2.37 (s, 3H).

2-Hydroxy-4-(3-methylphenoxy)benzoic Acid (18l) was prepared from acid 18k (177 mg, 0.7 mmol) in DCM (10 mL) treated with BBr$_3$ (3.5 mL, 1 M in DCM) at −20° C., warming to room temperature overnight. The reaction was quenched with and concentrated from methanol to yield 18l (175 mg, 99+%), used in the next reaction without further purification. $^1H$ NMR (CDCl$_3$) δ 10.51 (bs, 1H), 7.86 (d, 1H, J=8.9 Hz), 7.28 (t, 1H, J=7.7 Hz), 7.04 (d, 1H, J=7.5 Hz), 6.93-6.86 (m, 2H), 6.55 (dd, 1H, J=8.9, 2.2 Hz), 6.44 (d, 1H, J=2.3 Hz), 2.37 (s, 3H).

4-(2-Hydroxyphenoxy)-3-methoxybenzoic Acid (18m) was prepared according to General Procedure D in 24% yield following silica gel chromatography (methanol/DCM gradient). $^1H$ NMR (CDCl$_3$) δ 7.69 (s, 1H), 7.62 (d, 1H, J=8.4 Hz), 7.12-6.70 (m, 6H), 3.97 (s, 3H).

3-Chloro-4-(2-hydroxyphenoxy)benzoic Acid (18n) was prepared according to General Procedure D in 20% yield following a silica preparatory plate (5% isopropanol in DCM). $^1H$ NMR (CDCl$_3$) δ 8.22 (d, 1H, J=2.1 Hz), 7.92 (dd, 1H, J=8.5, 2.0 Hz), 7.21-7.05 (m, 2H), 6.98-6.77 (m, 4H).

4-(2-hydroxy-5-methylphenoxy)-3-methoxybenzoic acid (18o). The bromination of p-cresol, carried out via the method of Narender, et al.,[3] was followed by MOM protection[4] (96% yield over two steps). A solution of bis(pinacolato)diborane (2.5 g), dioxane (40 mL), KOAc (2.5 g) and the aryl bromide (6.5 mmol) was purged with nitrogen before Pd(dppf)Cl$_2$ (0.47 g) was added. The mixture was refluxed overnight. Silica chromatography (gradient to 20% EtOAc/hexanes) gave the boronate ester (1.93 g), which was dissolved in acetone (20 mL) and treated with a solution of Oxone (4 g) in H$_2$O (20 mL). After 10 min, NaHSO$_3$ was added and the resulting solution was extracted with EtOAc. Silica chromatography (gradient up to 15% EtOAc/hexanes) gave 2-(methoxymethoxy)-5-methylphenol (0.578 g, 53% over two steps). The diaryl ether was prepared from the phenol and appropriate 4-fluorobenzalde using General Procedure D. Silica chromatography (gradient up to 40% EtOAc/hexanes) gave the intermediate aldehyde (481 mg, 47%). The oxidation was followed by MOM cleavage with conc. HCl (0.25 mL) in 50% THF/iPrOH (10 mL) to yield 18o (391 mg, 89% over two steps). $^1H$ NMR (CDCl$_3$) δ 7.73-7.66 (m, 2H), 6.99-6.85 (m, 3H), 6.76 (s, 1H), 3.97 (s, 3H), 2.24 (s, 3H).

3-Chloro-4-(2-hydroxy-5-methylphenoxy)benzoic Acid (18p) was prepared according to General Procedure D from 2-methoxy-5-methylphenol and 3-chloro-4-fluorobenzaldehyde. The intermediate 3-chloro-4-(2-methoxy-5-methylphenoxy)benzoic acid product was treated with excess BBr$_3$ (1 M in DCM) at room temperature overnight. The resulting solution was quenched with and concentrated from methanol. The resulting oil was subjected to a silica preparatory plate (5% isopropanol in DCM) to yield 18p (162 mg, 58% over 3 steps). $^1H$ NMR (CDCl$_3$) δ 8.21 (s, 1H), 7.92 (d, 1H, J=8.0 Hz), 7.01-6.89 (m, 3H), 6.76 (s, 1H), 2.26 (s, 3H).

4-(2-Fluorophenoxy)-N-[(1S)-1-{[(3S)-4-(3-hydroxyphenyl)-3-methylpiperazin-1-yl]methyl}-2-methylpropyl] benzamide Dihydrochloride (19a). General Procedure B with acid 18a afforded 19a (37 mg, 64%) as a white powder: mp 156-159° C. (fusion), [α]$^{25}_D$ +64.6° (c 0.395, CH$_3$OH). Anal. (C$_{29}$H$_{36}$Cl$_2$FN$_3$O$_3$.H$_2$O) C, H, N. 19a free base: $^1H$ NMR (CDCl$_3$) δ 7.75 (d, 2H, J=8.7 Hz), 7.24-7.07 (m, 3H), 7.03 (t, 1H, J=8.0 Hz), 6.94 (d, 2H, J=8.7 Hz), 6.43-6.22 (m, 4H), 4.27-4.15 (m, 1H), 3.83-3.72 (m, 1H), 3.20-3.09 (m, 1H), 3.08-2.96 (m, 1H), 2.95-2.71 (m, 2H), 2.63-2.51 (m, 1H), 2.45-2.26 (m, 3H), 2.11-1.98 (m, 1H), 1.02-0.94 (m, 6H), 0.88 (d, 3H, J=6.4 Hz); $^{13}C$ NMR (CDCl$_3$) δ 167.2, 160.2, 157.1, 151.4, 129.9, 129.5, 128.8, 12.58, 125.0, 122.8, 117.4, 117.2, 116.4, 108.5, 106.3, 103.4, 58.5, 57.8, 54.5, 51.3, 50.9, 43.6, 30.8, 18.9, 18.0, 12.8; MS (ESI) m/z 492.5 (M+H)$^+$.

N-[(1S)-1-{[(3S)-4-(3-Hydroxyphenyl)-3-methylpiperazin-1-yl]methyl}-2-methylpropyl]-4-[3-(trifluoromethyl)phenoxy]benzamide (19b). General Procedure B with acid 18b afforded 19b (45 mg, 71%) as a white powder: mp 110-115° C. (fusion), [α]$^{25}_D$ +45.1° (c 0.27, CH$_3$OH). Anal. (C$_{30}$H$_{36}$Cl$_2$F$_3$N$_3$O$_3$.1.25H$_2$O) C, H, N. 19b free base: $^1H$ NMR (CDCl$_3$) δ 7.80 (d, 2H, J=8.7 Hz), 7.51-7.36 (m, 1H), 7.27 (s, 1H), 7.17 (d, 2H, J=7.6 Hz), 7.10-6.96 (m, 3H), 6.43-6.23 (m, 4H), 4.30-4.14 (m, 1H), 3.84-3.74 (m, 1H), $^{13}C$ NMR (CDCl$_3$) δ 167.2, 159.2, 157.1, 156.7, 151.4, 130.6, 130.4, 129.9, 129.1, 122.5, 120.6, 118.5, 116.2, 108.6, 106.5, 103.5, 58.5, 58.5, 57.8, 54.5, 51.4, 50.9, 43.6, 30.8, 18.9, 18.0, 12.8; MS (ESI) m/z 542.6 (M+H)$^+$.

4-(3-Chlorophenoxy)-N-[(1S)-1-{[(3S)-4-(3-hydroxyphenyl)-3-methylpiperazin-1-yl]methyl}-2-methylpropyl] benzamide Dihydrochloride (19c). General Procedure B with acid 18c afforded 19c (39 mg, 64%) as a white powder: mp 103-105° C. (fusion), [α]$^{25}_D$ +79.3° (c 0.145, CH$_3$OH). Anal. (C$_{29}$H$_{36}$Cl$_3$N$_3$O$_3$.1.5H$_2$O) C, H, N. 19c free base: $^1H$ NMR (CDCl$_3$) δ 7.78 (d, 2H, J=7.8 Hz), 7.26 (t, 1H, J=8.0 Hz), 7.15-6.84 (m, 5H), 6.50 (d, 1H, J=7.8 Hz), 6.43-6.25 (m, 3H), 4.31-4.16 (m, 1H), 3.82-3.70 (m, 1H), $^{13}C$ NMR (CDCl$_3$) δ 167.3, 159.4, 157.3, 157.1, 151.3, 135.3, 130.7, 130.0, 129.9, 129.0, 128.9, 124.2, 119.8, 118.5, 118.4, 117.6, 108.8, 106.7, 103.8, 58.5, 57.8, 54.4, 51.2, 50.9, 43.8, 30.9, 18.9, 18.1, 12.9; MS (ESI) m/z 508.5 (M+H)$^+$.

4-(3-Bromophenoxy)-N-[(1S)-1-{[(3S)-4-(3-hydroxyphenyl)-3-methylpiperazin-1-yl]methyl}-2-methylpropyl] benzamide Dihydrochloride (19d). General Procedure B with acid 18d afforded 19d (40 mg, 61%) as a white powder: mp 106-109° C. (fusion), [α]$^{25}_D$ +60.4° (c 0.23, CH$_3$OH). Anal. (C$_{29}$H$_{36}$BrCl$_2$N$_3$O$_3$.1.5H$_2$O) C, H, N. 19d free base: $^1$H NMR (CDCl$_3$) δ 7.78 (d, 2H, J=8.7 Hz), 7.31-7.13 (m, 2H), 7.09-6.91 (m, 4H), 6.44-6.23 (m, 4H), 4.29-4.14 (m, 1 $^{13}$C NMR (CDCl$_3$) δ 167.2, 159.4, 157.1, 151.4, 131.0, 123.0, 129.9, 127.1, 123.0, 122.6, 118.4, 118.0, 108.5, 106.4, 103.5, 58.5, 57.8, 54.5, 51.4, 50.9, 30.8, 18.9, 18.1, 12.8; MS (ESI) m/z 552.5 (M+H)$^+$.

4-(2-Hydroxy-3-methylphenoxy)-N-[(2S)-1-[(3S)-4-(3-hydroxyphenyl)-3-methylpiperazin-1-yl]-3-methylbutan-2-yl]benzamide Dihydrochloride (19e). General Procedure B with acid 18e afforded 19e (31.4 mg, 52%) as a white powder: mp 173° C. (fusion), [α]$^{25}_D$ 63.8° (c 0.24, CH$_3$OH). Anal. (C$_{30}$H$_{39}$Cl$_2$N$_3$O$_4$.1.5H$_2$O) C, H, N. 19e free base: $^1$H NMR (CDCl$_3$) δ 7.81-7.65 (m, 2H), 7.09-6.70 (m, 5H), 6.41-6.24 (m, 4H), 4.28-4.13 (m, 1H), 3.75-3.58 (m, 1H), 3.16-2.88 (m, 2H), 2.80-2.65 (m, 2H), 2.64-2.51 (m, 1H), 2.45-2.24 (m, 4H), 2.06-1.92 (m, 4H), 1.00-0.92 (m, 6H), 0.86-0.76 (m, 3H); $^{13}$C NMR (CDCl$_3$) δ 167.5, 157.1, 151.3, 149.0, 139.6, 132.0, 129.9, 129.0, 128.9, 128.6, 126.2, 122.7, 119.9, 117.2, 114.9, 114.5, 108.8, 103.7, 58.5, 54.4, 51.3, 50.9, 30.9, 18.9, 18.0, 16.1, 12.9; MS (ESI) m/z 504.6 (M+H)$^+$.

4-(3,5-Dimethylphenoxy)-N-[(1S)-1-{[(3S)-4-(3-hydroxyphenyl)-3-methylpiperazin-1-yl]methyl}-2-methylpropyl]benzamide Dihydrochloride (19f). General Procedure B using acid 18f afforded 19f (37 mg, 61%) as a white powder: mp 117-120° C. (fusion), [α]$^{25}_D$ +66.4° (c 0.66, CH$_3$OH). Anal. (C$_{31}$H$_{41}$Cl$_2$N$_3$O$_3$.2H$_2$O) C, H, N. 19f free base: $^1$H NMR (CDCl$_3$) δ 7.75 (d, 2H, J=8.7 Hz), 7.03 (t, 1H, J=8.0 Hz), 6.95 (d, 2H, J=8.7 Hz), 6.79 (s, 1H), 6.63 (s, 2H), 6.43-6.24 (m, 4H), 4.29-4.16 (m, 1H), 3.83-3.72 (m, 1H), 3.20-3.11 (m, 1H), 3.09-2.97 (m, 1H), 2.95-2.72 (m, 2H), 2.61 t, 1H, J=11 Hz), 2.51-2.30 (m, 3H), 2.28 (s, 6H), 2.11-1.98 (m, 1H), 1.03-0.93 (m, 6H), 0.88 (d, 3H, J=6.5 Hz); $^{13}$C NMR (CDCl$_3$) δ 166.2, 159.4, 156.0, 154.8, 150.2, 138.7, 128.7, 127.9, 127.6, 124.8, 116.6, 116.2, 107.4, 105.3, 102.4, 57.3, 56.7, 53.3, 50.1, 49.7, 42.4, 29.7, 20.1, 17.7, 16.9, 11.7; MS (ESI) m/z 502.8 (M+H)$^+$.

N-[(2S)-1-[(3S)-4-(3-Hydroxyphenyl)-3-methylpiperazin-1-yl]-3-methylbutan-2-yl]-3-methyl-4-(3-methylphenoxy)benzamide Dihydrochloride (19g). General Procedure B with acid 18g afforded 19g (42.9 mg, 70%) as a white powder: mp 124-130° C. (fusion), [α]$^{25}_D$ 46.6° (c 0.50, CH$_3$OH). Anal. (C$_{31}$H$_{41}$Cl$_2$N$_3$O$_3$.2H$_2$O) C, H, N. 19g free base: $^1$H NMR (CDCl$_3$) δ 7.68 (s, 1H), 7.55 (d, 2H, J=8.4 Hz), 7.19 (t, 1H, J=7.7 Hz), 7.03 (t, 1H, J=8.0 Hz), 6.91 (d, 1H, J=7.5 Hz), 6.81 (d, 1H, J=8.4 Hz), 6.75 (s, 1H), 6.42-6.28 (m, 5H), 4.29-4.15 (m, 1H), 3.84-3.72 (m, 1H), 3.15 (d, 1H, J=11.4 Hz), 3.03 (t, 1H, J=10.3 Hz), 2.84-2.72 (m, 2H), 2.65-2.53 (m, 1H), 2.47-2.32 (m, 3H), 2.31 (s, 3H), 2.27 (s, 3H) 2.12-1.98 (m, 1H), 1.02-0.95 (m, 6H), 0.90 (d, 3H, J=6.4 Hz); $^{13}$C NMR (CDCl$_3$) δ 167.6, 157.9, 157.2, 156.8, 151.4, 140.1, 130.3, 129.9, 129.7, 129.6, 129.5, 125.9, 124.2, 119.1, 118.1, 115.4, 108.5, 106.5, 103.6, 58.6, 58.6, 57.9, 54.5, 51.3, 50.9, 43.7, 43.7, 30.8, 21.4, 18.9, 18.1, 16.3, 12.8; MS (ESI) m/z 502.8 (M+H)$^+$.

N-[(2S)-1-[(3S)-4-(3-Hydroxyphenyl)-3-methylpiperazin-1-yl]-3-methylbutan-2-yl]-3-methoxy-4-(3-methylphenoxy)benzamide Dihydrochloride (19h). General Procedure B with acid 18h afforded 19h (46.7 mg, 75%) as a white powder: mp 128-131° C., [α]$^{25}_D$ 54.0° (c 0.73, CH$_3$OH). Anal. (C$_{31}$H$_{41}$Cl$_2$N$_3$O$_4$.2H$_2$O) C, H, N. 19h free base: $^1$H NMR (CDCl$_3$) δ 7.53 (d, 1H, J=1.9 Hz), 7.27-7.14 (m, 2H), 7.03 (t, 1H, J=8.0 Hz), 6.90 (d, 1H, J=7.6 Hz), 6.86 (d, 1H, J=8.3 Hz), 6.81-6.71 (m, 2H), 6.42-6.28 (m, 4H), 4.28-4.16 (m, 1H), 3.84 (s, 3H), 3.83-3.72 (m, 1H), 3.14 (d, 1H, J=11.8 Hz), 3.01 (t, 1H, J=10.7 Hz), 2.83-2.71 (m, 2H), 2.64-2.52 (m, 1H), 2.47-2.27 (m, 3H), 2.30 (s, 3H), 2.11-1.98 (m, 1H), 1.03-0.94 (m, 6H), 0.90 (d, 3H, J=6.4 Hz); $^{13}$C NMR (CDCl$_3$) δ 167.5, 157.3, 156.8, 151.4, 151.1, 148.7, 139.9, 130.8, 129.9, 129.4, 124.2, 119.1, 118.9, 118.9, 115.2, 112.3, 108.5, 106.6, 103.7, 101.6, 58.6, 57.9, 56.6, 54.5, 51.5, 50.9, 43.7, 30.8, 21.4, 19.0, 18.9, 18.1, 18.0, 14.2, 12.8; MS (ESI) m/z 518.7 (M+H)$^+$.

3-Hydroxy-N-[(2S)-1-[(3S)-4-(3-hydroxyphenyl)-3-methylpiperazin-1-yl]-3-methylbutan-2-yl]-4-(3-methylphenoxy)benzamide Dihydrochloride (19i). General Procedure B with acid 18i afforded 19i (38.6 mg, 64%) as a pale yellow powder: mp 195-200° C., [α]$^{25}_D$ 58.5° (c 1.07, CH$_3$OH). Anal. (C$_{30}$H$_{39}$Cl$_2$N$_3$O$_4$.1.5H$_2$O) C, H, N. 19i free base: $^1$H NMR (CDCl$_3$) δ 7.42 (s, 1H), 7.23-7.10 (m, 2H), 7.01 (t, 1H, J=7.8 Hz), 6.93 (d, 1H, J=7.4 Hz), 6.77 (s, 1H), 6.71 (t, 2H, J=8.7 Hz), 6.55 (bs, 1H), 6.45-6.32 (m, 3H), 4.33-4.19 (m, 1H), 3.52 (bs, 1H), 3.12-3.02 (m, 1H), 2.96-2.83 (m, 1H), 2.67-2.47 (m, 4H), 2.39-2.25 (m, 3H), 2.29 (s, 3H), 2.01-1.88 (m, 1H), 1.00-0.91 (m, 6H), 0.81 (d, 3H, J=6.3 Hz); $^{13}$C NMR (CDCl$_3$) δ 168.0, 157.3, 156.1, 151.5, 147.4, 146.9, 140.3, 131.1, 129.8, 129.7, 124.9, 119.2, 119.1, 119.1, 118.1, 115.7, 115.6, 107.7, 58.9, 53.9, 51.4, 51.2, 31.2, 21.4, 19.1, 19.1, 17.9, 13.8; MS (ESI) m/z 504.5 (M+H)$^+$.

N-[(1S)-1-{[(3S)-4-(3-Hydroxyphenyl)-3-methylpiperazin-1-yl]methyl}-2-methylpropyl]-2-methyl-4-(3-methylphenoxy)benzamide Dihydrochloride (19j). General Procedure B with acid 18j afforded 19j (13 mg, 22%) as a white powder: mp 164-167° C. (fusion), [α]$^{25}_D$ +46.6° (c 0.35, CH$_3$OH). Anal. (C$_{31}$H$_{41}$Cl$_2$N$_3$O$_3$.H$_2$O) C, H, N. 19j free base: $^1$H NMR (CDCl$_3$) δ 7.39 (d, 1H, J=8.2 Hz), 7.22 (t, 1H, J=8.0 Hz), 7.06 (t, 1H, J=8.0 Hz), 6.95 (d, 1H, J=7.4 Hz), 6.85-6.74 (m, 3H), 6.43 (dd, 1H, J=8.3, 1.6 Hz), 6.36 (s, 1H), 6.29 (dd, 1H, J=7.9, 1.8 Hz), 5.81 (bd, 1H, J=6.8 Hz), 4.30-4.16 (m, 1H), 3.89-3.77 (m, 1H), $^{13}$C NMR (CDCl$_3$) δ 169.8, 158.7, 156.9, 156.5, 151.5, 140.1, 138.7, 129.9, 129.6, 128.5, 124.6, 120.8, 120.0, 116.4, 115.4, 108.8, 106.3, 103.6, 59.4, 58.4, 54.6, 51.2, 51.0, 43.9, 30.6, 21.4, 20.2, 19.1, 17.8, 13.1; MS (ESI) m/z 502.8 (M+H)$^+$.

N-[(1S)-1-{[(3S)-4-(3-Hydroxyphenyl)-3-methylpiperazin-1-yl]methyl}-2-methylpropyl]-2-methoxy-4-(3-methylphenoxy)benzamide Dihydrochloride (19k). General Procedure B with acid 18k afforded 19k (35 mg, 58%) as a white powder: mp 99-102° C. (fusion), [α]$^{25}_D$ +82.3° (c 0.265, CH$_3$OH). Anal. (C$_{31}$H$_{41}$Cl$_2$N$_3$O$_4$.0.5H$_2$O) C, H, N. 19k free base: $^1$H NMR (CDCl$_3$) δ 8.11 (d, 1H, J=8.7 Hz), 7.83 (d, 1H, J=8.4 Hz), 7.29-7.19 (m, 1H), 7.07-6.95 (m, 2H), 6.89-6.80 (m, 2H), 6.64-6.53 (m, 2H), 6.42-6.26 (m, 3H), 4.37-4.25 (m, 1H), 3.89 (s, 3H), 3.82-3.70 (m, 1H), $^{13}$C NMR (CDCl$_3$) δ 165.1, 161.6, 158.9, 157.4, 155.7, 151.5, 140.2, 133.8, 129.8, 129.7, 125.2, 120.5, 116.9, 116.5, 110.2, 108.4, 106.4, 103.7, 101.7, 59.5, 58.7, 56.1, 54.0, 51.5, 51.1, 43.8, 43.8, 30.0, 21.4, 19.4, 17.3, 12.7; MS (ESI) m/z 518.7 (M+H)$^+$.

2-Hydroxy-N-[(1S)-1-{[(3S)-4-(3-hydroxyphenyl)-3-methylpiperazin-1-yl]methyl}-2-methylpropyl]-4-(3-methylphenoxy)benzamide Dihydrochloride (19l). General Procedure B with acid 18l afforded 19l (17 mg, 8.5%) as a white powder: mp 119-123° C. (fusion), [α]$^{25}_D$ +81.8° (c 0.08, CH$_3$OH). Anal. (C$_{30}$H$_{39}$Cl$_2$N$_3$O$_4$.EtOAc) C, H, N. 19l free base: ¹H NMR (CDCl₃) δ 7.70 (d, 1H, J=8.0 Hz), 7.54 (d, 1H, J=8.2 Hz), 7.23 (t, 1H, J=7.7 Hz), 7.12 (d, 1H, J=8.0 Hz), 7.06-6.95 (m, 2H), 6.88-6.78 (m, 2H), 6.46-6.25 (m, 5H), 4.37-4.17 (m, 1H), ¹³C NMR (CDCl₃) 163.5, 163.0, 157.2, 155.1, 140.2, 130.1, 129.6, 129.0, 126.0, 125.5, 121.1, 117.4, 108.8, 105.8, 57.8, 50.8, 31.2, 31.2, 21.3, 18.9, 18.3; MS (ESI) m/z 504.6 (M+H)⁺.

4-(2-Hydroxyphenoxy)-N-[(1S)-1-{[(3S)-4-(3-hydroxyphenyl)-3-methylpiperazin-1-yl]methyl}-2-methylpropyl]-3-methoxybenzamide Dihydrochloride (19m). General Procedure B using acid 18m afforded 19m (38.5 mg, 42%) as an off-white powder: mp 95-97° C. (fusion), [α]²⁵_D +55.2° (c 0.29, CH₃OH). Anal. (C₃₀H₃₉Cl₂N₃O₅·H₂O) C, H, N. 19m free base: ¹H NMR (CDCl₃) δ 7.50 (s, 1H), 7.20 (d, 1H, J=8.3 Hz), 7.06-6.98 (3H, m), 6.88-6.78 (m, 3H), 6.45-6.23 (m, 4H), 5.71 (bs, 2H), 4.29-4.14 (m, 1H), 3.79 (s, 3H), 3.75-3.62 (m, 1H), 3.15-2.24 (m, 8H), 2.07-1.93 (m, 1H), 1.01-0.93 (m, 6H), 0.85 (d, 3H, J=6.3 Hz); ¹³C NMR (CDCl₃) δ 167.4, 157.2, 151.4, 150.5, 148.6, 147.6, 143.7, 131.0, 129.9, 125.2, 125.2, 120.5, 119.1, 119.0, 118.4, 116.8, 116.7, 112.2, 108.8, 106.7, 103.8, 60.5, 58.6, 57.9, 56.1, 54.4, 51.5, 50.9, 43.9, 32.6, 30.9, 21.0, 18.9, 18.1, 14.2, 12.9; MS (ESI) m/z 520.6 (M+H)⁺.

3-Chloro-4-(2-hydroxyphenoxy)-N-[(1)-1-{[(3S)-4-(3-hydroxyphenyl)-3-methylpiperazin-1-yl]methyl}-2-methylpropyl]benzamide Dihydrochloride (19n). General Procedure B using acid 18n afforded 19n (23.4 mg, 26%) as a white powder: mp 153-157° C. (fusion), [α]²⁵_D +68° (c 0.053, CH₃OH). Anal. (C₂₉H₃₆Cl₃N₃O₄·0.5H₂O) C, H, N. 19n free base: ¹H NMR (CDCl₃) δ 7.83 (s, 1H), 7.55 (d, 1H, J=8.6 Hz), 7.12-6.99 (m, 3H), 6.88-6.78 (m, 3H), 6.44-6.21 (m, 4H), 4.26-4.11 (m, 1H), 3.74-3.62 (m, 1H), 3.16-2.91 (m, 2H), 2.78-2.65 (m, 2H), 2.64-2.50 (m, 1H), 2.49-2.26 (m, 3H), 2.09-1.94 (m, 1H), 1.00-0.93 (m, 6H), 0.82 (d, 3H, J=6.5 Hz); ¹³C NMR (CDCl₃) δ 166.1, 156.9, 155.2, 151.4, 147.6, 142.5, 123.0, 129.6, 126.8, 125.9, 120.8, 119.5, 117.9, 117.1, 109.0, 106.6, 58.4, 57.9, 54.4, 51.5, 50.9, 43.9, 30.9, 18.9, 18.1, 14.2, 13.0; MS (ESI) m/z 524.7 (M+H)⁺.

4-(2-Hydroxy-5-methylphenoxy)-N-[(1S)-1-{[(3S)-4-(3-hydroxyphenyl)-3-methylpiperazin-1-yl]methyl}-2-methylpropyl]-3-methoxybenzamide Dihydrochloride (19o). General Procedure B with acid 18o afforded 19o (49.8 mg, 53%) as a white powder: mp 100-103° C. (fusion), [α]²⁵_D +60.6° (c 0.18, CH₃OH). Anal. (C₃₁H₄₁Cl₂N₃O₅·H₂O) C, H, N. 19o free base: ¹H NMR (CDCl₃) δ 7.49 (d, 1H, J=1.7 Hz), 7.21 (dd, 1H, J=8.3, 1.7 Hz), 7.01 (t, 1H, J=8.3 Hz), 6.92-6.78 (m, 3H), 6.69-6.66 (m, 1H), 6.46-6.28 (m, 4H), 4.29-4.14 (m, 1H), 3.79 (s, 3H), 3.75-3.63 (m, 1H), 3.15-2.81 (m, 2H), 2.72 (d, 2H, J=10.2 Hz), 2.57 (t, 1H, J=11.2 Hz), 2.50-2.25 (m, 3H), 2.18 (s, 3H), 2.08-1.93 (m, 1H), 1.00-0.94 (m, 6H), 0.85 (d, 3H, J=6.4 Hz); ¹³C NMR (CDCl₃) δ 167.5, 157.2, 151.4, 150.5, 148.7, 145.2, 143.3, 130.9, 130.1, 129.9, 125.6, 119.7, 119.0, 118.3, 116.4, 116.4, 112.2, 108.7, 106.7, 103.8, 60.5, 58.6, 57.9, 56.1, 54.4, 51.5, 50.9, 43.9, 30.9, 21.0, 20.6, 19.0, 18.1, 14.2, 12.9; MS (ESI) m/z 534.3 (M+H)⁺.

3-Chloro-4-(2-hydroxy-5-methylphenoxy)-N-[(1S)-1-{[(3S)-4-(3-hydroxyphenyl)-3-methylpiperazin-1-yl]methyl}-2-methylpropyl]benzamide Dihydrochloride (19p). General Procedure B using acid 18p afforded 19p (29.0 mg, 31%) as a white powder: mp 145-148° C. (fusion), [α]²⁵_D +76° (c 0.073, CH₃OH). Anal. (C₃₀H₃₈Cl₃N₃O₄·H₂O) C, H, N. 19p free base: ¹H NMR (CDCl₃) δ 7.89 (s, 1H), 7.62 (d, 1H, J=8.2 Hz), 7.02 (t, 1H, J=8.0 Hz), 6.94 (d, 1H, J=7.9 Hz), 6.87 (d, 1H, J=8.2 Hz), 6.81 (d, 1H, J=8.6 Hz), 6.67 (s, 1H), 6.41-6.21 (m, 3H), 4.33-4.18 (m, 1H), ¹³C NMR (CDCl₃) δ 166.2, 157.0, 155.4, 151.4, 145.2, 142.1, 130.7, 130.6, 129.9, 129.5, 126.8, 126.4, 124.4, 120.1, 117.8, 116.8, 108.9, 106.6, 103.7, 60.4, 58.5, 57.9, 54.4, 51.5, 50.9, 43.9, 30.9, 21.0, 20.6, 18.9, 18.1, 14.2, 13.0; MS (ESI) m/z 538.3 (M+H)⁺.

TABLE 2

Inhibition of Agonist Stimulated [³⁵S]GTPγS Binding in Cloned Human μ, δ, and κ-Opioid Receptors for Compounds 19

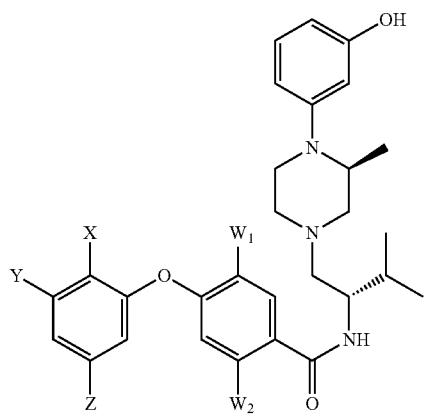

| RTI-5989- | compd | X, Y, Z, W₁, W₂ | μ, DAMGO $K_e$ (nM)$^a$ | δ, DPDPE $K_e$ (nM)$^a$ | κ, U69,593 $K_e$ (nM)$^a$ | μ/κ | δ/κ |
|---|---|---|---|---|---|---|---|
| 340 | 19a | F, H, H, H, H | 21.6 ± 4 | 96 ± 18 | 0.76 ± 0.21 | 28 | 126 |
| 342 | 19b | H, CF₃, H, H, H | 21 ± 7.2 | 54 ± 19 | 1.2 ± 0.35 | 18 | 45 |
| 343 | 19c | H, Cl, H, H, H | 18 ± 7.2 | 8.3 ± 0.9 | 0.42 ± 0.05 | 43 | 20 |
| 341 | 19d | H, Br, H, H, H | 17 ± 6.3 | 42 ± 19 | 0.48 ± 0.02 | 35 | 88 |
| 338 | 19e | OH, CH₃, H, H, H | 23.8 ± 8.9 | 92.7 ± 14 | 0.34 ± 0.16 | 70 | 272 |
| 339 | 19f | H, CH₃, CH₃, H, H | 25 ± 7 | 78 ± 20 | 0.98 ± 0.06 | 26 | 80 |
| 337 | 19g | H, CH₃, H, CH₃, H | 14.4 ± 3.9 | 21 ± 6.0 | 0.16 ± 0.03 | 89 | 131 |
| 336 | 19h | H, CH₃, H, OCH₃, H | 35.1 ± 15 | 93 ± 4 | 0.25 ± 0.07 | 140 | 372 |
| 334 | 19i | H, CH₃, H, OH, H | 13.7 ± 5.6 | 81 ± 35 | 0.57 ± 0.14 | 24 | 142 |

TABLE 2-continued

Inhibition of Agonist Stimulated [$^{35}$S]GTPγS Binding in Cloned Human μ, δ, and κ-Opioid Receptors for Compounds

19

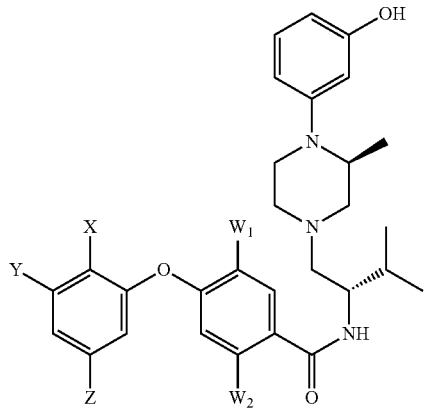

| RTI-5989- | compd | X, Y, Z, W$_1$, W$_2$ | μ, DAMGO K$_e$ (nM)$^a$ | δ, DPDPE K$_e$ (nM)$^a$ | κ, U69,593 K$_e$ (nM)$^a$ | μ/κ | δ/κ |
|---|---|---|---|---|---|---|---|
| 345 | 19j | H, CH$_3$, H, H, CH$_3$ | 14 ± 3 | 18 ± 3 | 0.65 ± 0.2 | 22 | 28 |
| 344 | 19k | H, CH$_3$, H, H, OCH$_3$ | 49 ± 14 | 63 ± 20 | 1.3 ± 0.03 | 38 | 48 |
| 347 | 19l | H, CH$_3$, H, H, OH | 145 ± 48 | 233 ± 90 | 1.8 ± 0.30 | 81 | 129 |
| 358 | 19m | OH, H, H, OCH$_3$, H, | 74 ± 23 | 67 ± 47 | 16.3 ± 2.7 | 5 | 4 |
| 351 | 19n | OH, H, H, Cl, H | 36 ± 9.2 | 210 ± 82 | 5.0 ± 0.82 | 7 | 42 |
| 359 | 19o | OH, H, CH$_3$, OCH$_3$, H | 10 ± 2.6 | 37 ± 13 | 6.2 ± 2.2 | 2 | 6 |
| 352 | 19p | OH, H, CH$_3$, Cl, H | 8.2 ± 1.7 | 15 ± 3.6 | 3.0 ± 1.1 | 3 | 5 |

$^a$None of the compounds showed agonist activity at 10 μM.

Obviously, numerous modifications and variations of the present invention are possible in light of the above teachings. It is therefore to be understood that within the scope of the appended claims, the invention may be practiced otherwise than as specifically described herein.

REFERENCES CITED (1) Dhawan, B. N.; Cesselin, F.; Raghubir, R.; Reisine, T.; Bradley, P. B.; Portoghese, P. S.; Hamon, M. International Union of Pharmacology. XII. Classification of opioid receptors. *Pharmacol. Rev.* 1996, 48, 567-592.
(2) Aldrich, J. V.; Vigil-Cruz, S. C. Narcotic Analgesics. In *Burger's Medicinal Chemistry and Drug Discovery*; 6th ed.; Abraham, D. J., Ed.; John Wiley & Sons: New York, N.Y., 2003; Vol. 6, Chapter 7, pp 329-481.
(3) Husbands, S. M. Kappa-opioid receptor ligands. *Expert Opin. Ther. Patents* 2004, 14, 1725-1741.
(4) Prisinzano, T. E.; Tidgewell, K.; Harding, W. W. Kappa opioids as potential treatments for stimulant dependence. *AAPS J.* 2005, 7, E592-E599.
(5) Metcalf, M. D.; Coop, A. Kappa opioid antagonists: past successes and future prospects. *AAPS J* 2005, 7, E704-E722.
(6) Carroll, F. I.; Thomas, J. B.; Dykstra, L. A.; Granger, A. L.; Allen, R. M.; Howard, J. L.; Pollard, G. T.; Aceto, M. D.; Harris, L. S. Pharmacological properties of JDTic: A novel κ-opioid receptor antagonist. *Eur. J. Pharmacol.* 2004, 501, 111-119.
(7) Thomas, J. B.; Atkinson, R. N.; Vinson, N. A.; Catanzaro, J. L.; Perretta, C. L.; Fix, S. E.; Mascarella, S. W.; Rothman, R. B.; Xu, H.; Dersch, C. M.; Cantrell, B. E.; Zimmerman, D. M.; Carroll, F. I. Identification of (3R)-7-hydroxy-N-((1S)-1-[[(3R,4R)-4-(3-hydroxyphenyl)-3,4-dimethyl-1-piperidinyl]methyl]-2-methylpropyl)-1,2,3,4-tetrahydro-3-isoquinolinecarboxamide as a novel potent and selective opioid kappa receptor antagonist. *J. Med. Chem.* 2003, 46, 3127-3137.
(8) Thomas, J. B.; Atkinson, R. N.; Rothman, R. B.; Fix, S. E.; Mascarella, S. W.; Vinson, N. A.; Xu, H.; Dersch, C. M.; Lu, Y.; Cantrell, B. E.; Zimmerman, D. M.; Carroll, F. I. Identification of the first trans-(3R,4R)-dimethyl-4-(3-hydroxyphenyl)piperidine derivative to possess highly potent and selective opioid kappa receptor antagonist activity. *J Med Chem* 2001, 44, 2687-2690.
(9) Kreek, M. J.; LaForge, K. S.; Butelman, E. Pharmacotherapy of addictions. *Nat. Rev. Drug Discov.,* 2002, 1, 710-726.
(10) Zimmerman, D. M.; Nickander, R.; Horng, J. S.; Wong, D. T. New structural concepts for narcotic antagonists defined in a 4-phenylpiperidine series. *Nature* 1978, 275, 332-334.
(11) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and mu receptor subtype-selectivity in (+)-(3R, 4R)-dimethyl-4-(3-hydroxyphenyl)piperidine opioid antagonists. *J Med Chem* 1998, 41, 1980-1990.
(12) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993, 36, 2833-2841.
(13) Mitch, C. H.; Leander, J. D.; Mendelsohn, L. G.; Shaw, W. N.; Wong, D. T.; Cantrell, B. E.; Johnson, B. G.; Reel, J. K.; Snoddy, J. D.; Takemori, A. E.; Zimmerman, D. M. 3,4-Dimethyl-4-(3-hydroxyphenyl)piperidines: Opioid antagonists with potent anorectant activity. *J. Med. Chem.* 1993, 36, 2842-2850.

(14) Zimmerman, D. M.; Gidda, J. S.; Cantrell, B. E.; Schoepp, D. D.; Johnson, B. G.; Leander, J. D. Discovery of a potent, peripherally selective trans-3,4-dimethyl-4-(3-hydroxyphenyl)piperidine opioid antagonist for the treatment of gastrointestinal motility disorders. *J. Med. Chem.* 1994, 37, 2262-2265.

(15) Delaney, C. P.; Yasothan, U.; Kirkpatrick, P. Alvimopan. *Nat. Rev. Drug Discov.* 2008, 7, 727-728.

(16) Statnick, M. A.; Suter, T. M.; Gackenheimer, S. L.; Emmerson, P. J.; Quimby, S. J.; Gehlert, D. R.; Wheeler, W. J.; Mitch, C. H. Na+-dependent high affinity binding of [3H]LY515300, a 3,4-dimethyl-4-(3-hydroxyphenyl) piperidine opioid receptor inverse agonist. *Eur. J. Pharmacol.* 2003, 482, 139-150.

(17) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of an opioid κ receptor subtype-selective N-substituent for (+)-(3R,4R)-dimethyl-4-(3-hydroxyphenyl)piperidine. *J. Med. Chem.* 1998, 41, 5188-5197.

(18) Beardsley, P. M.; Howard, J. L.; Shelton, K. L.; Carroll, F. I. Differential effects of the novel kappa opioid receptor antagonist, JDTic, on reinstatement of cocaine-seeking induced by footshock stressors vs cocaine primes and its antidepressant-like effects in rats. *Psychopharmacology (Berl)* 2005, 183, 118-126.

(19) Knoll, A. T.; Meloni, E. G.; Thomas, J. B.; Carroll, F. I.; Carlezon, W. A., Jr. Anxiolytic-Like Effects of κ-Opioid Receptor Antagonists in Models of Unlearned and Learned Fear in Rats. *J. Pharmacol. Exp. Ther.* 2007, 323, 838-845.

(20) Carroll, F. I.; Cueva, J. P.; Thomas, J. B.; Mascarella, S. W.; Runyon, S. P.; Navarro, H. A. 1-substituted 4-(3-hydroxyphenyl)piperazines are pure opioid receptor antagonists. *Med. Chem. Lett.* 2010, 1, 365-369.

(21) Brugel, T. A.; Smith, R. W.; Balestra, M.; Becker, C.; Daniels, T.; Hoerter, T. N.; Koether, G. M.; Throner, S. R.; Panko, L. M.; Folmer, J. J.; Cacciola, J.; Hunter, A. M.; Liu, R.; Edwards, P. D.; Brown, D. G.; Gordon, J.; Ledonne, N. C.; Pietras, M.; Schroeder, P.; Sygowski, L. A.; Hirata, L. T.; Zacco, A.; Peters, M. F. Discovery of 8-azabicyclo[3.2.1]octan-3-yloxy-benzamides as selective antagonists of the kappa opioid receptor. Part 1. *Bioorg Med Chem Lett* 2010, 20, 5847-5852.

(22) Peters, M. F.; Zacco, A.; Gordon, J.; Maciag, C. M.; Litwin, L. C.; Thompson, C.; Schroeder, P.; Sygowski, L. A.; Piser, T. M.; Brugel, T. A. Identification of short-acting kappa-opioid receptor antagonists with anxiolytic-like activity. *Eur J Pharmacol* 2011, 661, 27-34.

(23) Buezo, N. D.; Pedregal-Tercero, C.; McKinzie, D. L.; Mitch, C. H. Eli Lilly and Company. Kappa selective opioid receptor antagonist. U.S. Pat. No. 7,709,522 B2, 2010.

(24) Mague, S. D.; Pliakas, A. M.; Todtenkopf, M. S.; Tomasiewicz, H. C.; Zhang, Y.; Stevens, W. C., Jr.; Jones, R. M.; Portoghese, P. S.; Carlezon, W. A., Jr. Antidepressant-like effects of kappa-opioid receptor antagonists in the forced swim test in rats. *J. Pharmacol. Exp. Ther.* 2003, 305, 323-330.

(25) McLaughlin, J. P.; Marton-Popovici, M.; Chavkin, C. Kappa opioid receptor antagonism and prodynorphin gene disruption block stress-induced behavioral responses. *J. Neurosci.* 2003, 23, 5674-5683.

(26) Redila, V. A.; Chavkin, C. Stress-induced reinstatement of cocaine seeking is mediated by the kappa opioid system. *Psychopharmacology (Berl)* 2008, 200, 59-70.

(27) Carey, A. N.; Borozny, K.; Aldrich, J. V.; McLaughlin, J. P. Reinstatement of cocaine place-conditioning prevented by the peptide kappa-opioid receptor antagonist arodyn. *Eur. J. Pharmacol.* 2007, 569, 84-89.

(28) Walker, B. M.; Koob, G. F. Pharmacological evidence for a motivational role of κ-opioid systems in ethanol dependence. *Neuropsychopharmacology* 2007, 33, 643-652.

(29) Bodnar, R. J.; Glass, M. J.; Ragnauth, A.; Cooper, M. L. General, mu and kappa opioid antagonists in the nucleus accumbens alter food intake under deprivation, glucoprivic and palatable conditions. *Brain Res.* 1995, 700, 205-212.

(30) Bortolato, M.; Aru, G. N.; Frau, R.; Orru, M.; Fa, M.; Manunta, M.; Puddu, M.; Mereu, G.; Gessa, G. L. Kappa opioid receptor activation disrupts prepulse inhibition of the acoustic startle in rats. *Biol. Psychiatry* 2005, 57, 1550-1558.

(31) Benesh, D. R.; Blanco-Pillado, M.-J. Preparation of 4-(5-Aminomethyl)indole-1-ylmethyl)benzamide Derivatives as Opioid Receptor Antagonists for the Treatment of Obesity, PCT Int. Appl. WO 2005 90,303. 2005.

(32) McHardy, S.; Liras, S.; Guediche, S.; Coe, J. W. 4-Phenyl-piperidine Compounds and Their Use as Modulators of Opioid Receptors, US Patent Application Publication No. 204/0204453 A1. 2004.

(33) Faivre, V.; Roizard, D.; Brembilla, A.; Lochon, P. Synthesis of long-chain picolinic derivatives. *Bull. Soc. Chim. Fr.* 1991, 2, 278-285.

(34) Evans, D. A.; Katz, J. L.; West, T. R. Synthesis of Diaryl Ethers through the Copper-Promoted Arylation of Phenols with Arylboronic Acids. An Expedient Synthesis of Thyroxine. *Tetrahedron Lett.* 1998, 39, 2937-2940.

The invention claimed is:

1. A compound represented by the formula:

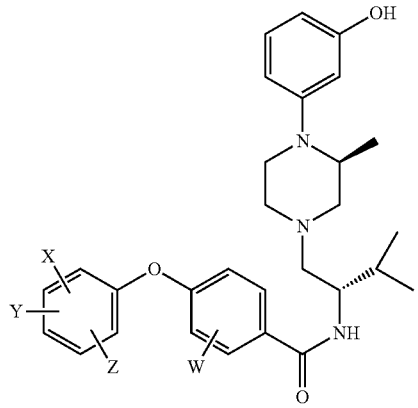

wherein

W, X, Y and Z are, independently, hydrogen, $C_{1-3}$ alkyl, $OC_{1-3}$ alkyl, F, OH, Br, Cl, CN, $CF_3$, $NO_2$, $SO_2CH_3$, $SO_2CF_3$ or $SO_2NH_2$.

2. The compound of claim 1, wherein W, X, Y and Z are, independently, hydrogen, methyl, methoxy, F, Cl or OH.

3. The compound of claim 1, wherein W, V, X, Y and Z are, independently, hydrogen, methyl, Cl or OH.

4. The compound of claim 1, wherein W is hydrogen, methyl or Cl.

5. The compound of claim 1, wherein X is hydrogen, methoxy or OH.

6. The compound of claim 1, wherein Y is hydrogen, methyl or methoxy.

7. The compound of claim 1, wherein Z is hydrogen, F, methyl or methoxy.

8. The compound of claim 1, which is represented by the formula:

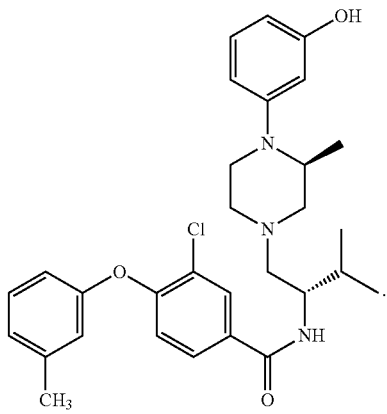 [SMILES: Cc1cccc(Oc2ccc(C(=O)N[C@H](CN3CCN(c4cccc(O)c4)[C@@H](C)C3)C(C)C)cc2Cl)c1]

9. The compound of claim 1, which is represented by the formula:

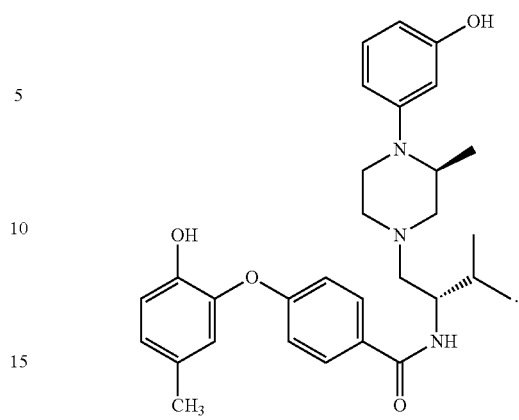

10. The compound of claim 1, which is a pharmaceutically acceptable salt.

11. A pharmaceutical composition, comprising the compound of claim 1 and a pharmaceutically acceptable carrier.

* * * * *

UNITED STATES PATENT AND TRADEMARK OFFICE
CERTIFICATE OF CORRECTION

PATENT NO. : 9,512,105 B2
APPLICATION NO. : 14/364003
DATED : December 6, 2016
INVENTOR(S) : Frank Ivy Carroll et al.

It is certified that error appears in the above-identified patent and that said Letters Patent is hereby corrected as shown below:

In Column 17, Line 333:
"H, OH, H, H, $CH_3$" should read -- H, OH, H, $CH_3$ --.

In Column 28, Line 40:
"12.58," should read -- 125.8 --.

Signed and Sealed this
Eighth Day of May, 2018

Andrei Iancu
*Director of the United States Patent and Trademark Office*